(12) United States Patent
Elliott et al.

(10) Patent No.: US 12,150,958 B2
(45) Date of Patent: Nov. 26, 2024

(54) COMPOSITIONS AND METHODS FOR TREATMENT OF AMYOTROPHIC LATERAL SCLEROSIS (ALS) AND OTHER NEURODEGENERATIVE DISEASES, AND ASSOCIATED METHODS FOR PREPARING SAID COMPOSITIONS

(71) Applicant: The Sallie Astor Burdine Breast Foundation, Baton Rouge, LA (US)

(72) Inventors: Robert L. Elliott, Baton Rouge, LA (US); Xianpeng Jiang, Baton Rouge, LA (US); Brent M. Segal, Pembroke, MA (US)

(73) Assignee: The Sallie Astor Burdine Breast Foundation, Baton Rouge, LA (US)

( * ) Notice: Subject to any disclaimer, the term of this patent is extended or adjusted under 35 U.S.C. 154(b) by 565 days.

(21) Appl. No.: 16/937,388

(22) Filed: Jul. 23, 2020

(65) Prior Publication Data
US 2021/0205358 A1  Jul. 8, 2021

Related U.S. Application Data

(60) Provisional application No. 62/958,592, filed on Jan. 8, 2020.

(51) Int. Cl.
| | |
|---|---|
| *A61K 35/12* | (2015.01) |
| *A61K 47/02* | (2006.01) |
| *A61K 47/18* | (2017.01) |
| *A61K 47/20* | (2006.01) |
| *A61K 47/26* | (2006.01) |
| *A61K 47/42* | (2017.01) |
| *A61P 25/28* | (2006.01) |

(52) U.S. Cl.
CPC .............. *A61K 35/12* (2013.01); *A61K 47/02* (2013.01); *A61K 47/183* (2013.01); *A61K 47/20* (2013.01); *A61K 47/26* (2013.01); *A61K 47/42* (2013.01); *A61P 25/28* (2018.01)

(58) Field of Classification Search
None
See application file for complete search history.

(56) References Cited

U.S. PATENT DOCUMENTS

| | | | |
|---|---|---|---|
| 9,855,296 B2 | 1/2018 | Cataldo et al. | |
| 2006/0234927 A1* | 10/2006 | Youdim | .......... A61P 43/00 514/6.9 |
| 2011/0008310 A1* | 1/2011 | Cataldo | .......... A01K 67/0271 424/94.4 |
| 2018/0057610 A1 | 3/2018 | McCully et al. | |
| 2018/0071337 A1 | 3/2018 | Cataldo et al. | |
| 2020/0009198 A1 | 1/2020 | Choi et al. | |

FOREIGN PATENT DOCUMENTS

| | | |
|---|---|---|
| CA | 2973885 A1 | 1/2018 |
| JP | 2019-507729 A | 3/2019 |
| WO | WO-2017/117249 A1 | 7/2017 |
| WO | WO-2018/101708 A1 | 6/2018 |
| WO | WO-2019/060297 A1 | 3/2019 |
| WO | WO-2021/141637 A1 | 7/2021 |

OTHER PUBLICATIONS

Choi (Ann. NY Acad. Sci. (2005), vol. 1042, pp. 88-100) (Year: 2005).*
Fleischer (Methods in Enzymology (1979), vol. LV, pp. 28-32) (Year: 1979).*
Goetz (In Vitro (1979), vol. 15, No. 2, pp. 114-119).*
Norat, P. et. al., Mitochondrial dysfunction in neurological disorders: Exploring mitochondrial transplantation, npj, Regenerative Medicine, 5:22 (2020).
Brestoff, J.R. et al., Intercellular Mitochondria Transfer to Macrophages Regulates White Adipose Tissue Homeostasis and Is Impaired in Obesity, Cell Metab., 33(2):270-282, (2021).
Hosseinian, S. et al., Prospects of mitochondrial transplantation in clinical medicine: Aspirations and challenges, 65:33-44, (2022).
Southard, J.H., and Belzer, F.O., New concepts in organ preservation, Clin Transplant. 7(1 part 2):134-7 (1993).
Alpert, N.M., et al., Quantitative in vivo mapping of myocardial mitochondrial membrane potential, Plos One 13(1):1-16, (2018).
Beaudart, C., et al., Assessment of Muscle Function and Physical Performance in Daily Clinical Practice, Calcified Tissue International, 105:1-14, (2019).
Boston Childrens Hospital, Transplantation of Autologously Derived Mitochondria Following Ischemia, 6 Pages (2016) [Online] Clinical Trial Identifier: NCT02851758 [https://clinicaltrials.gov/ct2/show/NCT02851758] [retrieved on Sep. 29, 2020].
Burgmann, H., et. al., The calcium chelating capacity of different protecting solutions. Transplantation, 54(6):1106-8, (1992).
Cammarata, A., Quantification of Mitochondrial Membrane Potential in the Isolated Rat Lung Using R6G, (2019).

(Continued)

*Primary Examiner* — Susan Hoffman
(74) *Attorney, Agent, or Firm* — Choate, Hall & Stewart LLP; William R. Haulbrook; Samuel R. Polio

(57) ABSTRACT

The present disclosure provides, among other things, methods for the treatment of neurodegenerative diseases (ND) and other mitochondrial disorders, and compositions related thereto. Described herein are in vitro (cell culture) and in vivo (animal model) experimental examples demonstrating mitochondrial organelle transplantation (MOT) for the treatment of NDs such as amyotrophic lateral sclerosis (ALS). Furthermore, as discussed herein, MOT has been performed in five human ALS patients with positive results—measurable improvement of their conditions has been observed, with no adverse events.

26 Claims, 15 Drawing Sheets
(1 of 15 Drawing Sheet(s) Filed in Color)
Specification includes a Sequence Listing.

(56) References Cited

OTHER PUBLICATIONS

Chang, JC, et al., Allogeneic/xenogeneic transplantation of peptide-labeled mitochondria in Parkinson's disease: restoration of mitochondria functions and attenuation of 6-hydroxydopamine-induced neurotoxicity. Transl Res. 170:40-56, (2016).
Chang, JC, et. al., Functional recovery of human cells harbouring the mitochondrial DNA mutation MERRF A8344G via peptide-mediated mitochondrial delivery, Neurosignals, 21(3-4):160-73, (2013).
Chazotte, B., Labeling mitochondria with MitoTracker dyes, Cold Spring Harb Protoc., 2011(8):990-2, (2011).
Clark, M., and Shay, J.W. Mitochondrial transformation of mammalian cells, Nature, 295(5850):605-7, (1982).
Corcelli, A., et al., Mitochondria isolated in nearly isotonic KCl buffer: focus on cardiolipin and organelle morphology, Biochim Biophys Acta, 1798(3):681-7, (2010).
Elliot, RL, and Jiang, XP, Head JF. Mitochondria organelle transplantation: introduction of normal epithelial mitochondria into human cancer cells inhibits proliferation and increases drug sensitivity, Breast Cancer Research Treatment, 136(2):347-54, (2012).
Elliot, RL, and Jiang, XP, The adverse effect of gentamicin on cell metabolism in three cultured mammary cell lines: "Are cell culture data skewed?" PLoS One, 14(4):e0214586, (2019).
Fürst, D., et. al., HLA Matching in Unrelated Stem Cell Transplantation up to Date, Transfus Med Hemother, 46:326-336, (2019).
Garnjobst, L., et. al., A cytoplasmic character in neurospora crassa, The Role of Nuclei and Mitochondria, J Cell Biol, 26 (2): 427-443, (1965).
Help Me Understand Genetics: Gene Groups, https://ghr.nlm.nih.gov/primer/genefamily/hla, (2019).
Huang P.J., et. al., Transferring Xenogenic Mitochondria Provides Neural Protection Against Ischemic Stress in Ischemic Rat Brains, Cell Transplant, 25(5):913-27, (2016).
Jiang, X., et al., Mitochondrial Toxicity of Azithromycin Results in Aerobic Glycolysis and DNA Damage of Human Mammary Epithelia and Fibroblasts, Antibiotics (Basel), 8(3):1-17, (2019).
King, M.P., and Attardi, G., Injection of mitochondria into human cells leads to a rapid replacement of the endogenous mitochondrial DNA, Cell, 52(6):811-9, (1988).
Knowles, J.K.C., An improved microinjection technique in Paramecium Aurelia: Transfer of mitochondria conferring erythromycin-resistance. Experimental Cell Research, 88:79-87, (1974).
Kong, J., and Xu, Z. Massive mitochondrial degeneration in motor neurons triggers the onset of amyotrophic lateral sclerosis in mice expressing a mutant SOD1, J Neurosci, 18(9):3241-50, (1998).
Lesage, S. et. al., Loss of VPS13C function in autosomal-recessive parkinsonism causes mitochondrial dysfunction and increases PINK1/Parkin-dependent mitophagy, Am. J. Hum. Genet. 98(3):500-513(2016).
Lucas C., et. al., The effect of respiration buffer composition on mitochondrial metabolism and function, Plos One, 12(11): e0187523, (2017).
Marklund, S., et al., Measuring and monitoring skeletal muscle function in COPD: current perspectives, Int J. Chron Obstruct Pulmon Dis, 14:1825-1838, (2019).
McCully J.D, et. al., Injection of isolated mitochondria during early reperfusion for cardioprotection, Am J Physiol Heart Circ Physiol, 296(1):H94-H105, (2009).
Mukhopadhyay, A., et. al., Binding of mitochondrial leader sequences to Tom20 assessed using a bacterial two-hybrid system shows that hydrophobic interactions are essential and that some mutated leaders that do not bind Tom20 can still be imported, Protein Sci., 15(12): 2739-2748, (2006).
Murphy, M.P., Mitochondrial Dysfunction Indirectly Elevates ROS Production by the Endoplasmic Reticulum, Cell Metabolism, 18(2):145-146, (2013).
Nicolson, G.L., Mitochondrial Dysfunction and Chronic Disease: Treatment with Natural Supplements, Integr Med. (Encinitas), 13(4):35-43, (2014).

Preble, J.M, et. al., Rapid isolation and purification of mitochondria for transplantation by tissue dissociation and differential filtration, J Vis Exp, (91):e51682, (2014).
Shi, X., et. al., Intravenous administration of mitochondria for treating experimental Parkinson's disease, Mitochondrion, 34:91-100, (2017).
Sirvandzade, F. et. al., Analysis of the Mitochondrial Membrane Potential Using the Cationic JC-1 Dye as a Sensitive Fluorescent Probe, Bio Protoc, 9(1): e3128, (2019).
Spees, J.L., et. al., Mitochondrial transfer between cells can rescue aerobic respiration, Proc Natl Acad Sci U S A., 103(5):1283-8, (2006).
Vives, E., et. al., A Truncated HIV-1 Tat Protein Basic Domain Rapidly Translocates through the Plasma Membrane and Accumulates in the Cell Nucleus, Journal of Biological Chemistry, 272(25):16010-7, (1997).
Wollenman, L.C., et. al., The effect of respiration buffer composition on mitochondrial metabolism and function, Plos one, 12(11): e0187523, (2017).
Xu, YJ et. al., The potential health benefits of taurine in cardiovascular disease, Exp Clin Cardiol, 13(2):57-65, (2008).
Jiang, X.P., et. al., Mitochodria Dynamically Transplant into cells in Vitro and in mice and rescue aerobic respiration of mitochondrial DNA-Depleted motor neuron NSC-34, J. Biomedical Science and Engineering, 13(9):203-221, (2020).
Elliot. R.L. and Jiang, X.P., Concern for Mitochondrial transplantation in Humans: "Another Opinion", Cardiovascular Surgery International, (1) Article 1007:25-26, (2020).
International Search Report for PCT/US20/47359 filed Aug. 21, 2020, 5 pages, (Feb. 5, 2021).
Written Opinion for PCT/US20/47359 filed Aug. 21, 2020, 9 pages, (Feb. 5, 2021).
Baucom, C. C. and Jiang, X.P., Mitochondrial Organelle Transplantation Is a Potential Therapeutic for Mitochondria Dysfunction in Severe Acute Respiratory Syndrome (SARS) Coronavirus Diseases, Scientific Research Publishing, Advances in Infectious Diseases, 11:298-309, (2021).
Bagheri, H.S. et al., Mitochondrial donation in translational medicine; from imagination to reality, J. Transl. Med., 18(1):367 (2020).
Chang, J.C. et al., Intranasal delivery of mitochondria for treatment of Parkinson's Disease model rats lesioned with 6-hydroxydopamine, Sci. Rep., 11(1):10597 (2021).
Cloer, C.M. et al., Mitochondrial transplant after ischemia reperfusion promotes cellular salvage and improves lung function during ex-vivo lung perfusion, J. Heart Lung Transplant., 42(5):575-584 (2023).
D'Amato, M. et al., Mitochondrial Transplantation in Mitochondrial Medicine: Current Challenges and Future Perspectives, Int. J. Mol. Sci., 24(3):1969 (2023).
Elliott, R. L. et al., Mitochondria and Neurodegeneration Could Mitochondrial Organelle Transfer be a Cellular Biotherapy for Neurodegenerative Diseases?, SOJ Biochemistry, 2(1):1-5 (2016).
Elliott, R. L. et al., Mitochondria Organelle Transplantation: The Mitochondrion, An Intracellular Organelle for Cell-Based Therapy, Opinion Commentary, Int J Applied Sci and Technology, 4:158-162 (2014).
Elliott, R. L. et al., Neurodegeneration and Mitochondria Organelle Transplantation: A Technology That Proof of Principle Suggest Is Ready for Prime Time, Neuroscience & Medicine, 11: 108-118 (2020).
Jia, X. et al., Mitochondrial transplantation ameliorates hippocampal damage following status epilepticus, Animal Model Exp. Med., 6(1):41-50 (2023).
Jiang, X. P. et al., Normal mitochondrial transplantation may be useful for the treatment of mitochondria-associated neurodegenerative diseases: evidences in vitro. J Neuromuscular Disease, 3(Suppl. 1):S215 (2016).
Kitani, T. et al., Internalization of isolated functional mitochondria: involvement of macropinocytosis, J. Cell. Mol. Med., 18(8):1694-1703 (2014).
Lin, M.W. et al., Mitochondrial Transplantation Attenuates Neural Damage and Improves Locomotor Function After Traumatic Spinal Cord Injury in Rats, Front. Neurosci., 16:800883 (2022).

(56) References Cited

OTHER PUBLICATIONS

Liu, D. et al., Intercellular mitochondrial transfer as a means of tissue revitalization, Signal Transduct. Target Ther., 6(1):65 (2021).
Pandya, J.D. et al., Comprehensive evaluation of mitochondrial redox profile, calcium dynamics, membrane integrity and apoptosis markers in a preclinical model of severe penetrating traumatic brain injury, Free Radic. Biol. Med., 198:44-58 (2023).
Park, A. et al., Mitochondrial Transplantation as a Novel Therapeutic Strategy for Mitochondrial Diseases, Int. J. Mol. Sci., 22(9):4793 (2021).
Prasuhn, J. et al., Targeting Mitochondrial Impairment in Parkinson's Disease: Challenges and Opportunities, Front. Cell. Dev. Biol., 8:615461 (2021).
Ramirez-Barbieri, G. et al., Alloreactivity and allorecognition of syngeneic and allogeneic mitochondria, Mitochondrion, 46:103-115 (2019).
Sun, X. et al., Intravenous Transplantation of an Ischemic-specific Peptide-TPP-mitochondrial Compound Alleviates Myocardial Ischemic Reperfusion Injury, ACS Nano., 17(2):896-909 (2023).
Xie, Q. et al., Mitochondrial Transplantation Attenuates Cerebral Ischemia-Reperfusion Injury: Possible Involvement of Mitochondrial Component Separation, Oxid. Med. Cell. Longev., 2021:1006636 (2021).
Yamada, Y. et al., Challenges in Promoting Mitochondrial Transplantation Therapy, Int. J. Mol. Sci., 21(17):6365 (2020).
Zhang, T.G. and Miao, C.Y., Mitochondrial transplantation as a promising therapy for mitochondrial diseases, Acta. Pharm. Sin. B., 13(3):1028-1035 (2023).
Chang, C.Y. et al., Current progress of mitochondrial transplantation that promotes neuronal regeneration, Transl. Neurodegener., 8:17 (2019).
Elliot, R.L. et al., Antibiotic Overusage Causes Mitochondrial Dysfunction Which May Promote Tumorigenesis, Journal of Cancer Treatment and Research, 5(4):62-65 (2017).
Elliot, R.L. et al., Antibiotics Friend and Foe: "From Wonder Drug to Causing Mitochondrial Dysfunction, Disrupting Human Microbiome and Promoting Tumorigenesis", Int. J. Clin. Med., 9:182-186 (2018).
Hayakawa, K. et al., Extracellular Mitochondria for Therapy and Diagnosis in Acute Central Nervous System Injury, JAMA Neurol., 75(1):119-122 (2018).
Jiang, X., et. al., Mitochondrial Toxicity of Azithromycin Results in Aerobic Glycolysis and DNA Damage of Human Mammary Epithelia and Fibroblasts, Supplemental Material included, Antibiotics, 8:110 (2019).
Nakamura, Y. et al., Therapeutic use of extracellular mitochondria in CNS injury and disease, Exp. Neurol., 324:113114 (2020).
Nitzan, K. et al., Mitochondrial Transfer Ameliorates Cognitive Deficits, Neuronal Loss, and Gliosis in Alzheimer's Disease Mice, J. Alzheimers Dis., 72(2):587-604 (2019).
Roushandeh, A.M. et al., Mitochondrial transplantation as a potential and novel master key for treatment of various incurable diseases, Cryotechnology, 71(2):647-663 (2019).

* cited by examiner

COMPOSITIONS AND METHODS FOR TREATMENT OF AMYOTROPHIC LATERAL SCLEROSIS (ALS) AND OTHER NEURODEGENERATIVE DISEASES, AND ASSOCIATED METHODS FOR PREPARING SAID COMPOSITIONS

CROSS-REFERENCE TO PENDING APPLICATION

The present application claims priority to U.S. Provisional Patent Application No. 62/958,592, filed Jan. 8, 2020, the text of which is incorporated by reference herein in its entirety.

SEQUENCE LISTING

The instant application contains a Sequence Listing which has been submitted electronically in ASCII format and is hereby incorporated by reference in its entirety. Said ASCII copy, created on Sep. 9, 2020, is named 2013631-0003_SL.txt and is 6,453 bytes in size.

BACKGROUND

Mitochondrial dysfunction is associated with neurodegenerative diseases (ND) including amyotrophic lateral sclerosis (ALS). Researchers have tested the therapeutic efficacy of many mitochondrial targeted agents; however, results have been disappointing without significant impact on disease survival. Several groups have demonstrated mitochondrial transfer of isolated mitochondria to defective cells, but translation of this research to clinical application has been limited.

ALS, known as Lou Gehrig's disease, involves both upper and lower motor neuron degeneration. It has sporadic and familial variants, with the sporadic more common. The familiar form is due to mutation in Cu, Zn superoxide dismutase (SOD1). The motor neuron degeneration leads to skeletal muscle atrophy, paralysis and death.

Mitochondrial dysfunction is involved in multiple NDs, such as Parkinson's disease, Alzheimer's and Huntington's diseases. Mitochondria are dynamic vital intracellular organelles involved in many essential cell functions, for example, energy production, regulating reactive oxygen species (ROS), metabolism, cell signaling, apoptosis, autophagy, and iron metabolism. A small defect in any of these functions may cause mitochondrial dysfunction. For example, excessive ROS causes free radicals that result in oxidative damage to mitochondrial DNA (mtDNA) and iron-sulfur cluster degradation with concomitant disruption of membrane potential and a marked decrease in energy production. This cascade leads to death of the motor neurons.

Currently, no ND is curable, and the treatments that are available only manage symptoms or delay progression. Many NDs are highly debilitating, and current treatments are insufficient to provide satisfactory amelioration of the condition of patients with these diseases. There is a need for treatments that improve the condition of patients with NDs.

SUMMARY

The present disclosure provides, among other things, methods for the treatment of neurodegenerative diseases (ND) and other mitochondrial disorders, and compositions related thereto. Described herein are in vitro (cell culture) and in vivo (animal model) experimental examples demonstrating mitochondrial organelle transplantation (MOT) for the treatment of NDs such as amyotrophic lateral sclerosis (ALS). Furthermore, as discussed herein, MOT has been performed in five human ALS patients with positive results—measurable improvement of their conditions has been observed, with no adverse events.

Evidence is presented that confirms the protocols of mitochondrial isolation and storage described herein adequately purify and maintain viable mitochondria for subsequent mitochondrial organelle transplantation in cell lines and patients. Surprisingly, it has been found that mitochondria of human fibroblasts do not express HLA antigens; thus, human mitochondria may be used for allogeneic mitochondrial organelle transplantation without the need for a human leukocyte antigen (HLA)-matching donor. Moreover, it has been discovered that human fibroblast mitochondria enter into cells with defective mitochondria more readily than they enter healthy cells; thus, diseased tissues and organs uptake more fibroblast mitochondria than healthy tissues. Furthermore, it has been discovered that antibiotics (which have toxicity to mitochondria of mammalian cells) are not necessary to culture human fibroblasts for the isolation and storage of mitochondria to be used in the MOT treatment methods described herein. These discoveries, in combination with the details presented herein, have made possible the methods for the treatment of neurodegenerative diseases (ND) and other mitochondrial disorders, and compositions related thereto, which are described herein.

In one aspect, the invention is directed to a method for allogeneic transplantation of mitochondria in a human subject, said method comprising administering to said subject a composition (e.g., a pharmaceutical composition) comprising mitochondria isolated from a donor other than the subject.

In certain embodiments, the subject has a neurodegenerative disease or other condition associated with mitochondrial dysfunction (e.g., and wherein the method is performed to treat the disease or condition). In certain embodiments, the subject has a disease selected from the group consisting of amyotrophic lateral sclerosis (ALS), Parkinson's disease (PD), a PD-related disorder, Alzheimer's disease (AD), Lewy body dementia (LBD), dementia, muscular dystrophy (MD), a mitochondrial disorder, prion disease, motor neurone disease (MND), Huntington's disease (HD), multiple sclerosis (MS), spinocerebellar ataxia (SCA), spinal muscular atrophy (SMA), Friedreich's ataxia, Batten disease, and fatal familial insomnia. In certain embodiments, the subject has amyotrophic lateral sclerosis (ALS).

In certain embodiments, the composition further comprises a mitochondrial storing buffer having a potassium ion concentration safe for administration to humans (e.g., wherein said mitochondrial storing buffer comprises a pharmaceutically acceptable carrier).

In certain embodiments, the administering step comprises parenterally administering (e.g., by intramuscular and intravenous injection) at least one unit dose of said composition to said subject. In certain embodiments, the administering step comprises both intramuscular injection and intravenous injection of said composition to said subject.

In certain embodiments, the method further comprises isolating said mitochondria from said donor. In certain embodiments, isolating said donor mitochondria comprises preparing cell lysate from tissue (or other biological sample) of the donor via tissue dissociation (e.g., using a bead-tube shake homogenizer). In certain embodiments, isolating said donor mitochondria comprises using a mitochondrial isolation buffer comprising a serine protease inhibitor (e.g., phenylmethylsulfonyl fluoride (PMFS)) (e.g., to prevent or reduce damage of donor mitochondria from digestive enzymes). In certain embodiments, the method comprises isolating said donor mitochondria without using an antibiotic.

In certain embodiments, the donor and the subject are not an HLA (human leukocyte antigen) match [e.g., not an identical match (e.g., based on match of 8 or 10 tested HLA markers) and/or not a haploidentical match (e.g., based on match of 8 or 10 tested HLA markers), and/or of indeterminate match status (e.g., no HLA markers tested prior to the administering step)].

In certain embodiments, the composition administered to the subject does not comprise an antibiotic (e.g., and wherein the subject is not administered an antibiotic).

In certain embodiments, the composition comprises mitochondria isolated from human primary fibroblasts of the donor.

In certain embodiments, the method further comprises isolating the mitochondria from tissue of the donor (e.g., fibroblast mitochondria). In certain embodiments, the isolating step is conducting using a mitochondrial isolation buffer composition (e.g., a mitochondrial isolation buffer solution described herein). In certain embodiments, the method further comprises storing the isolated mitochondria at a temperature below −40° C. (e.g., below −60° C., below −70° C., or below −80° C., e.g., using liquid nitrogen).

In certain embodiments, the method comprises (e.g., further comprises) administering to the subject an iron-chelating agent (e.g., desferrioxamine or deferasirox).

In certain embodiments, the method comprises (e.g., further comprises) administering to the subject an antioxidant and/or a probiotic.

In certain embodiments, the composition is a pharmaceutical composition. In certain embodiments, the composition further comprises a pharmaceutically acceptable carrier. In certain embodiments, the mitochondria are a therapeutic agent of the composition, present in a therapeutically effective amount.

In another aspect, the invention is directed to a method for improving muscle function in a subject, said method comprising administering to said subject a composition (e.g., a pharmaceutical composition) comprising mitochondria (e.g., mitochondria isolated from a donor other than the subject) in an amount sufficient to improve muscle function. In certain embodiments, the composition further comprises a pharmaceutically acceptable carrier. In certain embodiments, the mitochondria are a therapeutic agent of the composition, present in a therapeutically effective amount.

In another aspect, where the muscle function of a subject has been reduced due to administration of one or more members of the group consisting of an antibiotic, an antimalarial, an antiviral, or another treatment that causes or may cause mitochondrial damage, the invention is directed to a method comprising administering to said subject a composition (e.g., a pharmaceutical composition) comprising mitochondria (e.g., mitochondria isolated from a donor other than the subject) in an amount sufficient to improve muscle function, e.g., where the muscle is associated with lung function.

In another aspect, where the muscle function of a subject has been reduced due to one or more members of the group consisting of (i) a lung-related disorder such as viral pneumonia, (ii) a coronavirus infection such as an infection of Severe Acute Respiratory Syndrome Coronavirus including SARS-Cov-1 or SARS-Cov-2 or a related strain, (iii) influenza, (iv) a related genetic disorder, (v) Chronic Obstructive Pulmonary Disease (COPD), and (vi) another disease or condition where mitochondrial damage occurs and/or is present, the invention is directed to a method comprising administering to said subject a composition (e.g., a pharmaceutical composition) comprising mitochondria (e.g., mitochondria isolated from a donor other than the subject) in an amount sufficient to improve muscle function, e.g., where the muscle is associated with lung function.

In another aspect, the invention is directed to a method for improving muscle function of a subject that has been reduced due to one or more members of the group consisting of (i) a lung-related disorder such as viral pneumonia, (ii) a coronavirus infection such as an infection of Severe Acute Respiratory Syndrome Coronavirus including SARS-Cov-1 or SARS-Cov-2 and related strains, influenza, a related genetic disorders, Chronic Obstructive Pulmonary Disease (COPD), or another disease or condition where mitochondrial damage occurs and/or is present, the method comprising administering to said subject a composition (e.g., a pharmaceutical composition) comprising mitochondria (e.g., mitochondria isolated from a donor other than the subject) in an amount sufficient to improve muscle function of the subject.

In another aspect, where an iron level of a subject measured as serum ferritin, e.g., in a range from 0.25 mg to 2.5 mg/mL, is higher than normal as understood by those skilled in the art, the invention is directed to a method comprising administering to said subject a composition (e.g., a pharmaceutical composition) comprising mitochondria (e.g., mitochondria isolated from a donor other than the subject) in an amount sufficient to improve muscle function, e.g., with or without administering (e.g., separately administering) one or more iron chelation compounds such as desferrioxamine (deferoxamine).

In another aspect, where a subject is being treated with a pharmaceutical agent such as hydroxychloroquine and/or chloroquine for indications accompanied by high Reactive Oxygen Species (ROS) such as rheumatoid arthritis, the invention is directed to a method comprising administering to said subject a composition (e.g., a pharmaceutical composition) comprising mitochondria (e.g., mitochondria isolated from a donor other than the subject) in an amount sufficient to improve muscle function.

In another aspect, the invention is directed to a method for treating a neurodegenerative disease or other condition associated with mitochondrial dysfunction in a subject in need thereof, said method comprising administering to said subject a composition (e.g., a pharmaceutical composition) comprising mitochondria (e.g., mitochondria isolated from a donor other than the subject) in an amount sufficient to treat said neurodegenerative disease or other condition. In certain embodiments, the composition further comprises a pharmaceutically acceptable carrier. In certain embodiments, the mitochondria are a therapeutic agent of the composition, present in a therapeutically effective amount.

In another aspect, the invention is directed to a method for treating amyotrophic lateral sclerosis (ALS) in a subject in need thereof, said method comprising administering to said subject a composition (e.g., a pharmaceutical composition) comprising mitochondria (e.g., mitochondria isolated from a donor other than the subject) in an amount sufficient to treat said ALS. In certain embodiments, the composition further comprises a pharmaceutically acceptable carrier. In certain embodiments, the mitochondria are a therapeutic agent of the composition, present in a therapeutically effective amount.

In another aspect, the invention is directed to a mitochondrial isolation buffer composition (e.g., an aqueous solution) (e.g., for use in performing a method described herein, e.g., for use in mitochondrial organelle transplantation), said composition comprising: a buffering agent [e.g., a zwitterionic sulfonic acid buffering agent, e.g., 4-(2-hydroxyethyl)-1-piperazineethanesulfonic acid (HEPES) or salt thereof, e.g., HEPES potassium salt, (K-HEPES)]; a chelating agent [e.g., ethylene glycol-bis(β-aminoethyl ether)-N,N,N',N'-tetraacetic acid (EGTA) or salt thereof, e.g., K-EGTA)]; a sugar (e.g., sucrose); an agent that acts as a membrane stabilizer and/or oxygen radical scavenger and/or binder of $Ca^{2+}$ and/or binder of free fatty acid (e.g., bovine serum albumin, BSA); and a serine protease inhibitor (e.g., phenylmethylsulfonyl fluoride (PMFS), also called phenylmethane sulfonyl fluoride) (e.g., wherein the composition further comprises isolated donor mitochondria, e.g., fibroblast mitochondria). In certain embodiments, the mitochondrial isolation buffer composition does not comprise an antibiotic.

In another aspect, the invention is directed to a mitochondrial storing buffer composition (e.g., an aqueous solution) (e.g., for use in performing a method described herein, e.g., for use in mitochondrial organelle transplantation), said composition comprising: one or more buffering agents [e.g., a zwitterionic sulfonic acid buffering agent, e.g., 4-(2-hydroxyethyl)-1-piperazineethanesulfonic acid (HEPES) or salt thereof, e.g., HEPES potassium salt, (K-HEPES)] [e.g., monopotassium phosphate ($KH_2PO_4$)]; a source of magnesium ion [e.g., magnesium chloride ($MgCl_2$)]; a chelating agent [e.g., ethylene glycol-bis(β-aminoethyl ether)-N,N,N',N'-tetraacetic acid (EGTA) or salt thereof, e.g., K-EGTA)]; a sugar (e.g., sucrose); an antioxidant [e.g., taurine]; a cytoprotective agent that binds to calcium ion [e.g., lactobionate or salt thereof, e.g., K-lactobionate]; and an agent that acts as a membrane stabilizer and/or oxygen radical scavenger and/or binder of $Ca^{2+}$ and/or binder of free fatty acid (e.g., bovine serum albumin, BSA) (e.g., wherein the composition further comprises isolated donor mitochondria, e.g., fibroblast mitochondria). In certain embodiments, the mitochondrial storing buffer composition does not comprise an antibiotic.

In another aspect, the invention is directed to a kit comprising a donor mitochondria composition (e.g., an aqueous composition) in a unit dosage effective to treat a neurodegenerative disease or other condition associated with mitochondrial dysfunction in a subject, said donor mitochondria composition comprising: mitochondria isolated from tissue of a donor (e.g., fibroblast mitochondria); one or more buffering agents [e.g., a zwitterionic sulfonic acid buffering agent, e.g., 4-(2-hydroxyethyl)-1-piperazineethanesulfonic acid (HEPES) or salt thereof, e.g., HEPES potassium salt, (K-HEPES)] [e.g., monopotassium phosphate ($KH_2PO_4$)]; a source of magnesium ion [e.g., magnesium chloride ($MgCl_2$)]; a chelating agent [e.g., ethylene glycol-bis(β-aminoethyl ether)-N,N,N',N'-tetraacetic acid (EGTA) or salt thereof, e.g., K-EGTA)]; a sugar (e.g., sucrose); an antioxidant [e.g., taurine]; a cytoprotective agent that binds to calcium ion [e.g., lactobionate or salt thereof, e.g., K-lactobionate]; and an agent that acts as a membrane stabilizer and/or oxygen radical scavenger and/or binder of $Ca^{2+}$ and/or binder of free fatty acid (e.g., bovine serum albumin, BSA).

In certain embodiments, the donor and the subject are not an HLA (human leukocyte antigen) match [e.g., not an identical match (e.g., based on match of 8 or 10 tested HLA markers) and/or not a haploidentical match (e.g., based on match of 8 or 10 tested HLA markers), and/or of indeterminate match status (e.g., no HLA markers tested prior to the administering step)].

In certain embodiments, the donor mitochondria composition does not comprise an antibiotic.

In certain embodiments, the kit comprises instructions for administration of the composition to a subject. In certain embodiments, the kit further comprises instructions for optimizing the dose (e.g., unit dose) and/or frequency and/or route of administration of the composition.

In certain embodiments, the kit comprises a mitochondrial isolation buffer composition (e.g., an aqueous solution), said mitochondrial isolation buffer composition comprising: a buffering agent [e.g., a zwitterionic sulfonic acid buffering agent, e.g., 4-(2-hydroxyethyl)-1-piperazineethanesulfonic acid (HEPES) or salt thereof, e.g., HEPES potassium salt, (K-HEPES)]; a chelating agent [e.g., ethylene glycol-bis(β-aminoethyl ether)-N,N,N',N'-tetraacetic acid (EGTA) or salt thereof, e.g., K-EGTA)]; a sugar (e.g., sucrose); an agent that acts as a membrane stabilizer and/or oxygen radical scavenger and/or binder of $Ca^{2+}$ and/or binder of free fatty acid (e.g., bovine serum albumin, BSA); and a serine protease inhibitor (e.g., phenylmethylsulfonyl fluoride (PMFS), also called phenylmethane sulfonyl fluoride) (e.g., wherein the composition further comprises isolated donor mitochondria, e.g., fibroblast mitochondria).

Limitations described with respect to one aspect of the invention may, in certain embodiments, be practiced with respect to another aspect of the invention. For example, limitations of claims that depend directly or indirectly from a certain independent claim presented herein serve as support for those limitations being presented in additional dependent claims of one or more other independent claims.

Throughout the description, where compositions are described as having, including, or comprising specific components, or where methods are described as having, including, or comprising specific steps, it is contemplated that, additionally, there are compositions of the present invention that consist essentially of, or consist of, the recited components, and that there are methods according to the present invention that consist essentially of, or consist of, the recited steps.

In certain embodiments, compositions described herein are used to treat a disease or condition. In certain embodiments, compositions described herein are used to prevent onset and/or progression of a disease or condition (e.g., ND), for example, in subjects who are susceptible to said disease or condition. In certain embodiments, a variant of one or more components of the compositions described herein is/are used in place of said one or more components.

It should be understood that the order of steps or order for performing certain action is immaterial so long as the invention remains operable. Moreover, two or more steps or actions may be conducted simultaneously.

The following description is for illustration and exemplification of the disclosure only, and is not intended to limit the invention to the specific embodiments described.

The mention herein of any publication, for example, in the Background section, is not an admission that the publication serves as prior art with respect to any of the claims presented herein. The Background section is presented for purposes of clarity and is not meant as a description of prior art with respect to any claim.

Definitions

A or An: The articles "a" and "an" are used herein to refer to one or to more than one (i.e., to at least one) of the grammatical object of the article. By way of example, "an element" refers to one element or more than one element.

Administration: As used herein, the term "administration" typically refers to the administration of a composition to a subject or system, for example to achieve delivery of an agent that is, is included in, or is otherwise delivered by, the composition. Non-limiting examples of administration include oral administration; parenteral administration (for example, by subcutaneous, intramuscular, intravenous or epidural injection as, for example, a sterile solution or suspension, or sustained-release formulation, etc.); topical application (for example, as a cream, ointment, patch or spray applied for example to skin, lungs, or oral cavity); intravaginal or intrarectal administration (for example, as a pessary, suppository, cream, or foam); ocular administration; nasal or pulmonary administration, etc.

Agent: As used herein, the term "agent" refers to an entity (e.g., for example, a cell, a component of a cell such as mitochondria or other organelle, a small molecule, a peptide, a polypeptide, a nucleic acid, a lipid, a polysaccharide, a complex, a combination, a mixture, a system, or a phenomenon such as heat, electric current, electric field, magnetic force, magnetic field, etc.).

Amelioration: As used herein, the term "amelioration" refers to the prevention, reduction, palliation, or improvement of a state of a subject. Amelioration includes, but does not require, complete recovery or complete prevention of a disease, disorder or condition.

Antibiotic: As used herein, the term "antibiotic" refers to an antibacterial substance such as penicillin, gentamicin, streptomycin, cephalosporin, ciprofloxacin, or the like, that is used to treat or prevent infections by killing or inhibiting the growth of bacterial in or on the body, that is administered orally, topically, or by injection, and that is isolated from cultures of certain microorganisms (such as fungi) or is of semi-synthetic or synthetic origin.

Biological Sample: As used herein, the term "biological sample" typically refers to a sample obtained or derived from a biological source (e.g., a tissue or organism or cell culture) of interest, as described herein. In some embodiments, e.g., as set forth herein, a biological source is or includes an organism, such as an animal or human. In some embodiments, e.g., as set forth herein, a biological sample is or include biological tissue or fluid. In some embodiments, e.g., as set forth herein, a biological sample can be or include cells, tissue (e.g., skin tissue, muscle, or other tissue), or bodily fluid. In some embodiments, e.g., as set forth herein, a biological sample can be or include blood, blood cells, cell-free DNA, free floating nucleic acids, ascites, biopsy samples, surgical specimens, cell-containing body fluids, sputum, saliva, feces, urine, cerebrospinal fluid, peritoneal fluid, pleural fluid, lymph, gynecological fluids, secretions, excretions, skin swabs, vaginal swabs, oral swabs, nasal swabs, washings or lavages such as a ductal lavages or bronchioalveolar lavages, aspirates, scrapings, bone marrow. In some embodiments, e.g., as set forth herein, a biological sample is or includes cells obtained from a single subject or from a plurality of subjects. A sample can be a "primary sample" obtained directly from a biological source, or can be a "processed sample." A biological sample can also be referred to as a "sample."

Improved, increased, or reduced: As used herein, these terms, or grammatically comparable comparative terms, indicate values that are relative to a comparable reference measurement. For example, in some embodiments, e.g., as set forth herein, an assessed value achieved with an agent of interest may be "improved" relative to that obtained with a comparable reference agent or with no agent. Alternatively or additionally, in some embodiments, e.g., as set forth herein, an assessed value in a subject or system of interest may be "improved" relative to that obtained in the same subject or system under different conditions or at a different point in time (e.g., prior to or after an event such as administration of an agent of interest), or in a different, comparable subject (e.g., in a comparable subject or system that differs from the subject or system of interest in presence of one or more indicators of a particular disease, disorder or condition of interest, or in prior exposure to a condition or agent, etc.). In some embodiments, e.g., as set forth herein, comparative terms refer to statistically relevant differences (e.g., differences of a prevalence and/or magnitude sufficient to achieve statistical relevance). Those of skill in the art will be aware, or will readily be able to determine, in a given context, a degree and/or prevalence of difference that is required or sufficient to achieve such statistical significance.

Neurodegenerative disease: As used herein, the term "neurodegenerative disease" (also referred to as "degenerative nerve disease") is an umbrella term for conditions which primarily affect the neurons in the human brain. In certain instances, neurodegenerative disease is characterized by a progressive loss of neurons associated with deposition of proteins showing altered physicochemical properties in the brain and/or in peripheral organs. Neurodegenerative diseases include, for example, amyotrophic lateral sclerosis (ALS), Parkinson's disease (PD) and PD-related disorders, Alzheimer's disease (AD), Lewy body dementia (LBD), other forms of dementia, muscular dystrophy (MD), mitochondrial disorders, prion diseases, motor neuron diseases (MND), Huntington's disease (HD), multiple sclerosis (MS), spinocerebellar ataxia (SCA), spinal muscular atrophy (SMA), Friedreich's ataxia, Batten disease, fatal familial insomnia, and others.

Pharmaceutical composition: As used herein, the term "pharmaceutical composition" refers to a composition in which an active agent is provided together with one or more pharmaceutically acceptable carriers. In some embodiments, e.g., as set forth herein, the active agent is present in a unit dose amount appropriate for administration to a subject, e.g., in a therapeutic regimen that shows a statistically significant probability of achieving a predetermined therapeutic effect when administered to a relevant population. In some embodiments, e.g., as set forth herein, a pharmaceutical composition can be formulated for administration in a particular form (e.g., in a solid form or a liquid form), and/or can be specifically adapted for, for example: oral administration (for example, as a drenche (aqueous or non-aqueous solutions or suspensions), tablet, capsule, bolus, powder, granule, paste, etc., which can be formulated specifically for example for buccal, sublingual, or systemic absorption); parenteral administration (for example, by subcutaneous, intramuscular, intravenous or epidural injection as, for example, a sterile solution or suspension, or sustained-release formulation, etc.); topical application (for example, as a cream, ointment, patch or spray applied for example to skin, lungs, or oral cavity); intravaginal or intrarectal administration (for example, as a pessary, suppository, cream, or foam); ocular administration; nasal or pulmonary administration, etc.

Pharmaceutically acceptable: As used herein, the term "pharmaceutically acceptable," as applied to one or more, or all, component(s) for formulation of a composition as disclosed herein, means that each component must be compatible with the other ingredients of the composition and not deleterious to the recipient thereof.

Pharmaceutically acceptable carrier: As used herein, the term "pharmaceutically acceptable carrier" refers to a pharmaceutically-acceptable material, composition, or vehicle, such as a liquid or solid filler, diluent, excipient, or solvent encapsulating material, that facilitates formulation and/or modifies bioavailability of an agent, e.g., a pharmaceutical agent. Some examples of materials which can serve as pharmaceutically-acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; pH buffered solutions; polyesters, polycarbonates and/or polyanhydrides; and other non-toxic compatible substances employed in pharmaceutical formulations.

Prevent or prevention: The terms "prevent" and "prevention," as used herein in connection with the occurrence of a disease, disorder, or condition, refers to reducing the risk of developing the disease, disorder, or condition; delaying onset of the disease, disorder, or condition; delaying onset of one or more characteristics or symptoms of the disease, disorder, or condition; and/or to reducing the frequency and/or severity of one or more characteristics or symptoms of the disease, disorder, or condition. Prevention can refer to prevention in a particular subject or to a statistical impact on a population of subjects. Prevention can be considered complete when onset of a disease, disorder, or condition has been delayed for a predefined period of time.

Prognosis: As used herein, the term "prognosis" refers to determining the qualitative or quantitative probability of at least one possible future outcome or event. As used herein, a prognosis can be a determination of the likely course of a disease, disorder, or condition such as cancer in a subject, a determination regarding the life expectancy of a subject, or a determination regarding response to therapy, e.g., to a particular therapy.

Reference: As used herein describes a standard or control relative to which a comparison is performed. For example, in some embodiments, e.g., as set forth herein, an agent, subject, animal, individual, population, sample, sequence, or value of interest is compared with a reference or control agent, subject, animal, individual, population, sample, sequence, or value. In some embodiments, e.g., as set forth herein, a reference or characteristic thereof is tested and/or determined substantially simultaneously with the testing or determination of the characteristic in a sample of interest. In some embodiments, e.g., as set forth herein, a reference is a historical reference, optionally embodied in a tangible medium. Typically, as would be understood by those of skill in the art, a reference is determined or characterized under comparable conditions or circumstances to those under assessment, e.g., with regard to a sample. Those skilled in the art will appreciate when sufficient similarities are present to justify reliance on and/or comparison to a particular possible reference or control.

Sample: As used herein, the term "sample" typically refers to an aliquot of material obtained or derived from a source of interest. In some embodiments, e.g., as set forth herein, a source of interest is a biological or environmental source. In some embodiments, e.g., as set forth herein, a sample is a "primary sample" obtained directly from a source of interest. In some embodiments, e.g., as set forth herein, as will be clear from context, the term "sample" refers to a preparation that is obtained by processing of a primary sample (e.g., by removing one or more components of and/or by adding one or more agents to a primary sample).

Susceptible to: An individual who is "susceptible to" a disease, disorder, or condition is at risk for developing the disease, disorder, or condition. In some embodiments, e.g., as set forth herein, an individual who is susceptible to a disease, disorder, or condition does not display any symptoms of the disease, disorder, or condition. In some embodiments, e.g., as set forth herein, an individual who is susceptible to a disease, disorder, or condition has not been diagnosed with the disease, disorder, and/or condition. In some embodiments, e.g., as set forth herein, an individual who is susceptible to a disease, disorder, or condition is an individual who has been exposed to conditions associated with, or presents a biomarker status associated with, development of the disease, disorder, or condition. In some embodiments, e.g., as set forth herein, a risk of developing a disease, disorder, and/or condition is a population-based risk (e.g., family members of individuals suffering from the disease, disorder, or condition).

Subject: As used herein, the term "subject" refers to an organism, typically a mammal (e.g., a human). In some embodiments, e.g., as set forth herein, a subject is suffering from a disease, disorder or condition. In some embodiments, e.g., as set forth herein, a subject is susceptible to a disease, disorder, or condition. In some embodiments, e.g., as set forth herein, a subject displays one or more symptoms or characteristics of a disease, disorder or condition. In some embodiments, e.g., as set forth herein, a subject is not suffering from a disease, disorder or condition. In some embodiments, e.g., as set forth herein, a subject does not display any symptom or characteristic of a disease, disorder, or condition. In some embodiments, e.g., as set forth herein, a subject is someone with one or more features characteristic of susceptibility to or risk of a disease, disorder, or condition. In some embodiments, e.g., as set forth herein, a subject is a patient. In some embodiments, e.g., as set forth herein, a subject is an individual to whom diagnosis has been performed and/or to whom therapy has been administered. In some instances, e.g., as set forth herein, a human subject can be interchangeably referred to as an "individual."

Therapeutic agent, pharmaceutical agent, and active agent: As used herein, the terms "therapeutic agent", "pharmaceutical agent", and "active agent" are interchangeable, and each refers to any agent that elicits a desired pharmacological effect when administered to a subject. In some embodiments, e.g., as set forth herein, an agent is considered to be a therapeutic agent if it demonstrates a statistically significant effect across an appropriate population. In some embodiments, e.g., as set forth herein, the appropriate population can be a population of model organisms or a human population. In some embodiments, e.g., as set forth herein, an appropriate population can be defined by various criteria, such as a certain age group, gender, genetic background, preexisting clinical conditions, etc. In some embodiments, e.g., as set forth herein, a therapeutic agent is a substance that can be used for treatment of a disease, disorder, or condition. In some embodiments, e.g., as set forth herein, a therapeutic agent is an agent that has been or is required to be approved by a government agency before it can be marketed for administration to humans. In some embodiments, e.g., as set forth herein, a therapeutic agent is an agent for which a medical prescription is required for administration to humans.

Therapeutically effective amount: As used herein, the term "therapeutically effective amount" refers to an amount that produces a desired effect for which it is administered. In some embodiments, e.g., as set forth herein, the term refers to an amount that is sufficient, when administered to a population suffering from or susceptible to a disease, disorder, or condition, in accordance with a therapeutic dosing regimen, to treat the disease, disorder, or condition. Those of ordinary skill in the art will appreciate that the term therapeutically effective amount does not in fact require successful treatment be achieved in a particular individual. Rather, a therapeutically effective amount can be an amount that provides a particular desired pharmacological response in a significant number of subjects when administered to individuals in need of such treatment. In some embodiments, e.g., as set forth herein, reference to a therapeutically effective amount can be a reference to an amount as measured in one or more specific tissues (e.g., a tissue affected by the disease, disorder or condition) or fluids (e.g., blood, saliva, serum, sweat, tears, urine, etc.). Those of ordinary skill in the art will appreciate that, in some embodiments, a therapeutically effective amount of a particular agent can be formulated and/or administered in a single dose. In some embodiments, e.g., as set forth herein, a therapeutically effective agent can be formulated and/or administered in a plurality of doses, for example, as part of a multi-dose dosing regimen.

Treatment: As used herein, the term "treatment" (also "treat" or "treating") refers to administration of a therapy that partially or completely alleviates, ameliorates, relieves, inhibits, delays onset of, halts progression of, slows progression of, reverses progression of, reduces severity of, and/or reduces incidence of one or more symptoms, features, and/or causes of a particular disease, disorder, or condition, or is administered for the purpose of achieving any such result. In some embodiments, e.g., as set forth herein, such treatment can be of a subject who does not exhibit signs of the relevant disease, disorder, or condition and/or of a subject who exhibits only early signs of the disease, disorder, or condition. Alternatively or additionally, such treatment can be of a subject who exhibits one or more established signs of the relevant disease, disorder and/or condition. In some embodiments, e.g., as set forth herein, treatment can be of a subject who has been diagnosed as suffering from the relevant disease, disorder, and/or condition. In some embodiments, e.g., as set forth herein, treatment can be of a subject known to have one or more susceptibility factors that are statistically correlated with increased risk of development of the relevant disease, disorder, or condition. In various examples, treatment is of a cancer.

Unit dose: As used herein, the term "unit dose" refers to an amount administered as a single dose and/or in a physically discrete unit of a pharmaceutical composition. In many embodiments, e.g., as set forth herein, a unit dose contains a predetermined quantity of an active agent. In some embodiments, e.g., as set forth herein, a unit dose contains an entire single dose of the agent. In some embodiments, e.g., as set forth herein, more than one-unit dose is administered to achieve a total single dose. In some embodiments, e.g., as set forth herein, administration of multiple unit doses is required, or expected to be required, in order to achieve an intended effect. A unit dose can be, for example, a volume of liquid (e.g., an acceptable carrier) containing a predetermined quantity of one or more therapeutic moieties, a predetermined amount of one or more therapeutic moieties in solid form, a sustained release formulation or drug delivery device containing a predetermined amount of one or more therapeutic moieties, etc. It will be appreciated that a unit dose can be present in a formulation that includes any of a variety of components in addition to the therapeutic agent(s). For example, acceptable carriers (e.g., pharmaceutically acceptable carriers), diluents, stabilizers, buffers, preservatives, etc., can be included. It will be appreciated by those skilled in the art, in many embodiments, e.g., as set forth herein, a total appropriate daily dosage of a particular therapeutic agent can comprise a portion, or a plurality, of unit doses, and can be decided, for example, by a medical practitioner within the scope of sound medical judgment. In some embodiments, e.g., as set forth herein, the specific effective dose level for any particular subject or organism can depend upon a variety of factors including the disorder being treated and the severity of the disorder; activity of specific active compound employed; specific composition employed; age, body weight, general health, sex and diet of the subject; time of administration, and rate of excretion of the specific active compound employed; duration of the treatment; drugs and/or additional therapies used in combination or coincidental with specific compound(s) employed, and like factors well known in the medical arts Variant: As used herein, the term "variant" refers to an entity that shows significant structural identity with a reference entity but differs structurally from the reference entity in the presence, absence, or level of one or more chemical moieties as compared with the reference entity. In some embodiments, e.g., as set forth herein, a variant also differs functionally from its reference entity. In general, whether a particular entity is properly considered to be a "variant" of a reference entity is based on its degree of structural identity with the reference entity. A variant can be a molecule comparable, but not identical to, a reference. For example, a variant peptide can differ from a reference peptide at one or more differences in the amino acid sequence. In some embodiments, e.g., as set forth herein, a variant peptide shows an overall sequence identity with a reference peptide that is at least 85%, 86%, 87%, 88%, 89%, 90%, 91%, 92%, 93%, 94%, 95%, 96%, 97%, or 99%.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The foregoing and other objects, aspects, features, and advantages of the present disclosure will become more apparent and better understood by referring to the following description taken in conjunction with the accompanying drawings, in which:

FIG. 3A, FIG. 3C: phase contrast; FIG. 3B, FIG. 3D: fluorescence; FIG. 3A, FIG. 3B: fibroblasts; FIG. 3A, FIG. 3D: isolated mitochondria from fibroblasts.

FIG. 6A: transplanted with NSC-34 mitochondria; FIG. 6B: transplanted with fibroblast mitochondria.

FIG. 12A: HLA-AB/C, green fluorescence is mainly seen on cell surface; FIG. 12B: mitochondria labeled by MitoTracker Red, red fluorescence is mainly in the cytoplasm.

FIG. 13A, FIG. 13B: NSC-34, FIG. 13A—phase contrast, FIG. 13B—fluorescence; FIG. 13C, FIG. 13D: EtBr-treated NSC-34, FIG. 13C—phase contrast, FIG. 13D—fluorescence.

DETAILED DESCRIPTION

Figure 1:
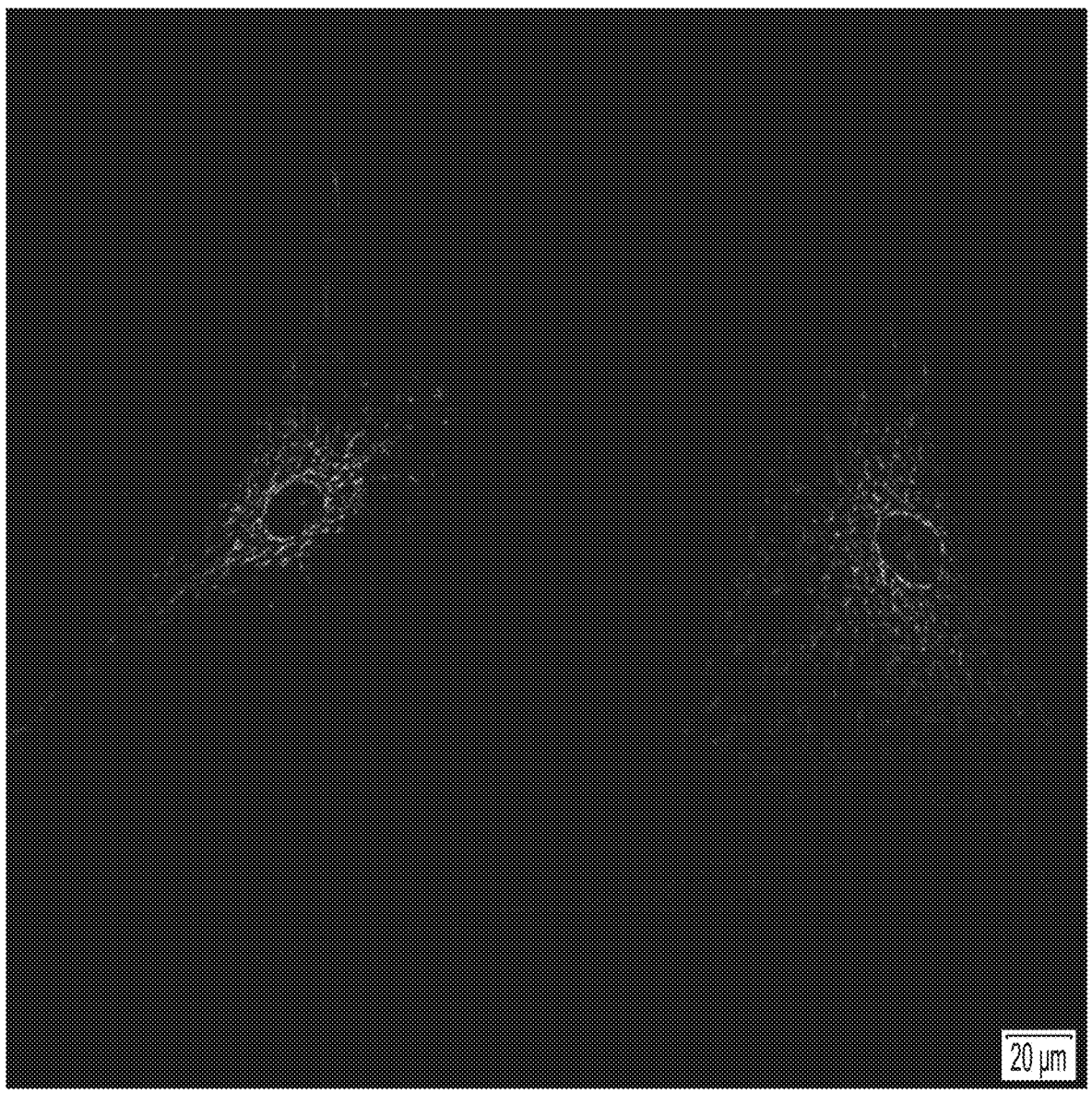
FIG. 1 is an image showing GFP-labelled mitochondria of fibroblasts, according to an illustrative embodiment. There are 337±80 mitochondria per human fibroblast. Mitochondria were counted and analyzed by Olympus IX83 fluorescent microscope and Cellsense software.

The methods and compositions described herein demonstrate the use of human primary fibroblasts as a source of donor mitochondria for treatment of amyotrophic lateral sclerosis (ALS), other neurodegenerative diseases such as Parkinson's disease and Alzheimer's disease, stroke, and other conditions and diseases that result in reduced muscle function due to mitochondrial damage. Fibroblasts share many characteristics with mesenchymal stem cells (MSCs), and it is found herein that allogeneic mitochondria from primary fibroblasts exhibit low or no immunogenicity and need no HLA tying match in mitochondrial transplantation. The mitochondrial respiration buffer (MRB) solutions described herein (also referred to herein as mitochondrial storing buffer compositions) maintain good viability of mitochondria and are safe for intravenous and intramuscular injection in human patients. In one embodiment, the MRB comprises 240 mM sucrose, 2 mM KH2PO4, 3 mM MgCl2, 10 mM K-HEPES, 1 mM K-EGTA, 20 mM taurine, 15 mM K-lactobionate, and 0.1% human serum albumin (HSA) at pH 7.2.

As discussed in further detail herein, dosage of mitochondria can be determined for a particular subject. The number of fibroblasts can be used to estimate mitochondrial number. In one embodiment, a starting mitochondrial dosage isolated from 50 millions of primary fibroblasts can be used.

For example, according to an illustrative clinical administered protocol for ALS patients, in a given treatment, half of the mitochondria from 50 million primary fibroblasts are injected intravenously, with the other half injected intramuscularly to multiple sites of diseased muscles. For example, in some embodiments, injections to the lower extremities are indicated if the disease mainly affects the lower extremities; and if symptoms mainly occur in upper extremities, such as with speech and swallowing muscles, the mitochondria are injected to the upper extremities and neck muscles.

In another example, according to an illustrative clinical administered protocol for a patient who is suffering from another neurodegenerative disease such as Parkinson's or Alzheimer's, or who has suffered a stroke, all the mitochondria from 50 million primary fibroblasts are injected intravenously.

As discussed in further detail herein, in addition to administration of mitochondria as part of mitochondrial organelle transplantation (MOT), the patient may be administered an iron-chelating agent (e.g., desferrioxamine or deferasirox), an antioxidant, and/or a probiotic. In some embodiments, administration of antibiotics is avoided due to potential deleterious effects on the transplanted mitochondria.

To prepare for mitochondrial transplantation study in human neurodegenerative diseases, human fibroblasts were selected as a mitochondrial donor, as fibroblasts share many characteristics with mesenchymal stromal cells (MSCs). Human primary fibroblasts were isolated and mitochondrial DNA (mtDNA)-depleted mouse motor neuron NSC-34 cells (NSC-34 ρ0 cells) were developed. The fibroblast and NSC-34 cell's mitochondria were co-cultured with NSC-34

ρ⁰ cells. Mitochondrial transplantation was observed by fluorescent microscopy. Gene expression was determined by polymerase chain reaction (PCR) and real time PCR (qPCR). Also, mitochondria were injected into mice bearing mammary adenocarcinoma 4T1 cells. The following results were found: 1) There are abundant mitochondria in fibroblasts (337±80 mitochondria per fibroblast). 42.4% of viable mitochondria were obtained by using differential centrifugation. The isolated mitochondria were actively transplanted into NSC-34 $\rho^0$ cells after co-culture; 2) Fibroblasts transfer mitochondria to human mammary adenocarcinoma MCF-7 cells; 3) There is no expression of HLA-I antigen in fibroblast's mitochondria indicating they can be used for allogeneic mitochondrial transplantation without HLA antigen match; 4) PCR and qPCR show that NSC-34 $\rho^0$ cells lose mitochondrially encoded cytochrome c oxidase I (MT-CO1) and mitochondrially encoded NADH dehydrogenase 1 (MT-ND1) and upregulate expression of glycolysis-associated genes hexokinase (HK2), glucose transporter 1 (SLC2A1) and lactate dehydrogenase A (LDHA); 5) Transplantation of NSC-34 mitochondria restores MT-CO1 and MT-ND1 and downregulates gene expression of HK2, SLC2A1 and LDHA; 6) Normal mammary epithelial mitochondria successfully enter to 4T1 cells in mice. Subcutaneous injection of mitochondria is safe for mice. Mitochondrial transplantation replenishes mtDNA and rescues aerobic respiration of diseased cells with mitochondrial dysfunction. Human primary fibroblasts are proper mitochondrial donor for mitochondrial transplantation study in human neurodegenerative diseases.

In eukaryotic cells, mitochondria generate ATP by oxidative phosphorylation (OXPHOS) in the presence of oxygen. Mitochondria also play an important role in synthesis of iron-sulfur (Fe—S) clusters, β-oxidation of fatty acids, synthesis of heme prosthetic groups, the urea cycle, as well as homeostasis of calcium, iron and reactive oxygen species (ROS). Mitochondria are highly dynamic organelles which frequently fuse and divide. Mitochondrial fusion/fission allow segregation of damaged mitochondria, mitophagy to remove damaged mitochondria, and ultimately cell death if the damage is too severe. In addition, mitochondria can transfer between cells. Cells may be able to obtain functional mitochondria from other cells in order to satisfy their bioenergetics and biosynthetic needs. Without wishing to be bound to any particular theory, the possible mechanisms include tunneling nanotubes, extracellular vesicles and partial or complete cell fusion.

Mitochondrial dysfunction contributes to many diseases such as neurodegenerative disease, cardiac disease and cancer. Mitochondrial dysfunction has been documented in amyotrophic lateral sclerosis (ALS), Alzheimer's disease (AD), and Parkinson's disease (PD), for example. Mitochondria are essential for neural function because neurons highly depend on aerobic OXPHOS in mitochondria for their energetic needs. Defective mitochondrial respiration and ATP production in neurons result in neural dysfunction and degeneration. Mitochondria also produce ROS. If oxidative stress of ROS overwhelms the antioxidative defense most from superoxide dismutase (SOD), catalase (CAT) and glutathione peroxidase (GPX), ROS causes protein, lipid and DNA damage of neurons. In addition, overload of mitochondrial calcium and iron impairs ATP production and structures of mitochondria and neurons. A few proteins from gene mutations have been linked to familial and sporadic ALS, including superoxide dismutase 1 (SOD1), TAR DNA binding protein (TARDBP; TDP-43), Fused in sarcoma (FUS), Chromosome 9 open reading frame 72 (C9orf72), and dipeptide repeat protein (DPR), which have been shown to interact with mitochondria in ALS mouse models and human patients.

Mitochondria are highly present in cardiac cells due to the increased energy demands of such cells. Mitochondrial dysfunction is associated with the development of numerous cardiac diseases such as atherosclerosis, ischemia-reperfusion injury, hypertension, cardiac hypertrophy and heart failure.

Defects in mitochondrial function have also been linked to tumorigenesis. For example, it has been observed that cancer cells have an increase in glycolysis and lactate production in the presence of oxygen without an increase in OXPHOS, known as the "Warburg Effect". Many cancers have mitochondrial defects and dysfunction. Glycolytic inhibitors have been found to suppress tumor growth in animal models and clinical trials.

Described below are experimental examples of mitochondrial transplantation (MT) to defective neurons and tumor cells in cell culture and mice, and safety of mitochondrial injection in mice. It was found that mitochondria transfer between human fibroblasts and breast cancer cells after co-culture. Mitochondria isolated from human fibroblasts are candidates for transplanting to mouse mtDNA-depleted neurons. Transplantation of mouse motor neural mitochondria replenishes mtDNA and rescues aerobic respiration of mouse mtDNA-depleted neurons. In addition, mitochondria isolated from mouse normal mammary epithelia are integrated into mammary adenocarcinoma cells in a mouse model Injection of exogenous mitochondria is safe for experimental mice.

Experimental Example I

Isolation, Primary Culture and Cryopreservation of Human Fibroblasts

All protocols used sterile techniques in a Class II, Type A2 laminar flow hood. All culture plastic materials and surgical scalpel were sterile and disposal. Human skin tissue was donated by a young healthy man who signed informed consent. Skin tissue was surgically collected in outpatient clinical center and dropped to a 50 ml disposal sterile centrifuge tube containing 15 ml of sterile 0.9% sodium chloride injection. Skin (0.5 cm×2 cm) was washed with cold sterile saline. Fat tissue was trimmed. The skin was cut to small pieces using a sterile disposal scalpel in a sterile disposal 100 mm culture dish. All tissue pieces and saline were transferred into a sterile glass chamber with cap and stir bar. 4.5 ml of 3% collagenase type 3 (Worthington Biochemical Corporation, Lakewood, N.J., USA) was added to the chamber. The final volume was 20 ml. The chamber was placed on a magnetic stirrer in 37° C. oven for digestion. The tissue was digested for 5 hours with gentle stirring until the tissue piece disappeared. The liquid was transferred into a sterile 50 ml centrifuge tube and centrifuged for 5 minutes at 400×g. The supernatant was aspirated. Then, the following was added: 20 ml pre-warmed (37° C.) complete alpha minimum essential media (alpha MEM) (GIBCO, Carlsbad, Calif., USA) containing 5% human platelet lysate (HPL) (Biological Industries, Cromwell, Conn., USA) and 0.05 mg/ml gentamicin (GIBCO, Carlsbad, Calif., USA). Then the cell pellet was re-suspended, and the cell suspension transferred to a 182 cm²-flask. The flask was cultured at 37° C. with 5% CO2 incubator overnight. The medium and floating cells were aspirated next day. 20 ml fresh medium was added to the flask. The flask was returned to the incubator for culture with medium refresh every 3-4 days.

When cells growth was 80% confluent, cells were subcultured to new flasks by 1:10 dilution. The primary fibroblasts of second and third passages were collected, re-suspended in Nutrifreez D10 cryopreservation medium (Biological Industries, Cromwell, Conn., USA), aliquoted to 1 ml containing $1\times10^6$ cells in cryovials, frozen and stored in liquid nitrogen.

Cell Cultures

Human mammary adenocarcinoma cell line MCF-7, mouse mammary adenocarcinoma cell line 4T1 and mouse mammary epithelium cell line EpH4-Ev were purchased from American Type Culture Collection (ATCC) (Manassas, Va., USA). MCF-7, 4T1 and human primary fibroblasts were recovered from liquid nitrogen and cultured in alpha MEM containing 10% fetal bovine serum (FBS) (GIBCO, Carlsbad, Calif., USA). EpH4-Ev cells were cultured in alpha MEM containing 10% FBS and 1.2 µg/mL puromycin (Sigma Aldrich, St. Louis, Mo., USA). NSC-34 is a hybrid cell line, produced by fusion of motor neuron enriched, embryonic mouse spinal cord cells with mouse neuroblastoma. NSC-34 was purchased from Cedarlane corporation (Ontario, Canada) and cultured in Dulbecco's modified eagle medium (DMEM) (GIBCO, Carlsbad, Calif., USA) containing 10% FBS. When cells grew to 80% full in flask, they were digested with TrypLE expression solution (GIBCO, Carlsbad, Calif., USA) and sub-cultured at 37° C. and 5% CO2.

Isolation of Mitochondria

Mitochondria were isolated by differential centrifugation. All reagents were sterile. Cells were harvested with TrypLe expression solution and pelleted by centrifugation for 5 minutes at 400×g and at 4° C. After aspiration of the solution and media, cell pellet was re-suspended in ice-cold 300 mM sucrose mitochondrial isolation buffer (MIB) (Sigma Aldrich, St. Louis, Mo., USA) and homogenized by bead beating (Bead Ruptor 12, Omni International homogenizer company (Kennesaw, Ga., USA). The cell lysate was centrifuged for 10 minutes at 700×g and at 4° C. Then, the supernatant was transferred to new centrifugation tubes and centrifuged for 10 minutes at 9,000×g and at 4° C. The supernatant was removed. The mitochondrial pellet was re-suspended with 240 mM sucrose mitochondrial respiration buffer (MRB) (Sigma Aldrich, St. Louis, Mo., USA). In order to determine the number of isolated mitochondria, 5 µl of JC-1-stained mitochondria was placed on glass slide and covered with 22 mm×22 mm coverslip (area $4.84\times10^8$ µm$^2$). The mitochondria were observed through 20× object lens, photographic pictures were taken in five fields and mitochondrial number was counted in each picture by Cellsense software of Olympus IX83 fluorescent microscope (Olympus, Tokyo, Japan). The object area of each picture was calculated by using the scale bar (µm) in the pictures. The number of mitochondria in 10 µl was calculated as the following: (coverslip area $4.84\times10^8$ µm$^2$÷object area in µm$^2$ per picture)×the average of mitochondrial number per picture. Then, the number of total isolated mitochondria was calculated.

Measurement of Mitochondrial Protein

Mitochondrial protein content can be used to estimate mitochondrial number. If the mitochondria were used for measurement of protein content, mitochondria were washed twice by protein-free MRB. The mitochondria were re-suspended and lysed by RIPA buffer (Thermofisher Scientific, Waltham, MA, USA). 1 ml of RIPA buffer was used for 40 mg ($\leq 5\times10^6$ cells) of wet pellet. The mitochondria were shaken gently for 30 minutes on ice. Then, the mitochondrial lysate was centrifuged at 14,000×g for 10 minutes to pellet debris. The supernatant was transferred to 1.5 ml vial for protein content measurement. The protein was quantitated by Pierce BCA protein assay kit (Thermo Scientific, Rockford, Ill., USA). The procedure follows the protocol of the assay kit. In brief, the instructions are to pipette 25 µl of standard or sample to the replicate wells, add 200 µl of BCR working reagent to each well and mix plate thoroughly for 30 seconds, incubate the plate at 37° C. for 30 minutes, cool down the plate to room temperature, and measure the absorbance at 562 nm on a plate reader. The protein concentrations of samples were calculated by four-parameter logistic curve.

Immunofluorescent Staining of Human Leukocyte Antigen I (HLA I) in Primary Fibroblasts and Mitochondria Twenty thousand (20,000) primary fibroblasts were cultured at glass bottom cell culture dishes overnight. Mitochondria were isolated from $5\times10^6$ fibroblasts. Fibroblasts in dishes and the mitochondria in 1.5 ml Eppendorf centrifugation tubes were fixed with 4% paraformaldehyde solution for 15 minutes at room temperature. The rabbit anti-human HLA-ABC polyclonal antibody (Thermofisher Scientific, Waltham, MA, USA) reacts to all types (HLA-A, -B and -C) of HLA I antigen (the abbreviation HLA means Human Leukocyte Antigen). The brief procedure of immunofluorescent staining is as following: wash twice with 1× phosphate buffered saline (PBS), block with 5% goat serum in 1×PBS, wash once, incubate with 200 µl 1:400 dilution of rabbit anti-human HLA-ABC polyclonal antibody overnight at 4° C., wash 3 times with 1×PBS, incubate with goat anti-rabbit IgG-Alexa 488 for 1 hour at room temperature, wash for 3 times with 1×PBS, add 300 µl of 1×PBS to the dishes and tubes, re-suspend the mitochondria in 1.5 ml Eppendorf tubes and add 100 µl of the mitochondria to the glass area of new glass bottom dishes, and observe fluorescence under Olympus IX83 fluorescent microscope. All pictures were taken with 1 second exposure.

Staining Mitochondria with JC-1 or MitoTracker Dyes

Mitochondrial membrane potential generated by proton pumps is found to be an important component in the process of energy storage during OXPHOS. Membrane potential dependent dyes such as JC-1(5,5',6,6'-tetrachloro-1,1',3,3'-tetraethylbenzimidazolocarbocyanine iodide) and MitoTracker dyes (rosamine- or cyCarbocyanine-based probes) have been used to stain mitochondria and monitor mitochondrial potential. For JC-1 staining, mitochondria were stained with a mitochondria staining kit (Sigma CS0390, St. Louis, Mo., USA). The brief procedure is as follows: mix 25 µl of 200×JC-1 Stock Solution in 4 mL of ultrapure water in a test tube; close the test tube and mix solution by inversion or vortex test tube briefly; incubate test tube for 2 min at room temperature to completely dissolve JC-1; open the test tube and add 1 ml of JC-1 Staining Buffer 5×; mix by inversion; then, mix the staining mixture with an equal volume of complete medium for cell growth; aspirate growth medium from flask and overlay cells with the above mixture; add 0.2-0.4 ml of the mixture per cm$^2$ of growth surface; incubate cells for 20 minutes at 37° C. in humidified atmosphere containing 5% CO$_2$; aspirate the mixture; then wash the cells twice with cold growth medium. Fluorescence was observed using an Olympus IX83 fluorescent microscope. In cells which maintain electrochemical potential gradient, the dye concentrated in mitochondria, where it formed bright red fluorescent aggregates (J-aggregates). If cells failed to maintain membrane potential, the JC-1 was dispersed through the entire cells resulting in a shift from red to green fluorescence (JC-1 monomers).

For MitoTracker dyes, culture media were aspirated. Cells were covered with fresh media containing 150 nM of MitoTracker Orange or Red dyes (Thermofisher Scientific, Waltham, MA, USA). and cultured for 30 minutes at 37° C. and 5% $CO_2$. Then, staining solution was removed. Cells were washed once, covered with fresh media, and observed under fluorescent microscope.

Mitochondrial Transfer Between Fibroblasts and Cancer MCF-7 Cells

CellLight Mitochondria-RFP or -GFP, BacMam 2.0 were purchased from Invitrogen (Carlsbad, Calif., USA). They are fluorescent and are currently the leader sequence of E1 alpha pyruvate dehydrogenase (in mitochondrial matrix) fusions that provide accurate and specific targeting to mitochondria in live-cell mitochondrial imaging. Cells grew on culture dishes to 70% confluence. The appropriate volume of CellLight reagent for the number of cells wewasre calculated as the protocol of the products. The volume of CellLight mitochondria-RFP or -GFP were added to cells. The cells were incubated at 37° C. at least 16 hours and observed by Olympus IX83 fluorescent microscope. The average number of mitochondria per fibroblast was determined by Cellsense software. In order to test mitochondrial transfer between adenocarcinoma cell MCF-7 and fibroblasts, mitochondria of MCF-7 and fibroblasts were labelled with CellLight Mitochondria-RFP or -GFP, respectively, for at least 16 hours. The media were removed. Cells were washed twice with prewarmed fresh media and dis-attached with TrypLE express reagent. The same number of MCF-7 and fibroblasts were mixed and co-cultured at 37° C. and 5% CO2 for 24 hours. The fluorescence in cells was observed by Olympus IX83 fluorescent microscope.

Depleting Mitochondrial DNA of NSC-34 by Ethidium Bromide

Long-term treatment of cells with low doses (0.1-2 μg/ml) of ethidium bromide (EtBr), an inhibitor of DNA/RNA synthesis, is thought to specifically suppress the replication and transcription of extrachromosomal genetic components such as mtDNA without affecting nuclear DNA replication and transcription. NSC-34 cells were maintained in the complete DMEM medium containing 2 μg/ml EtBr and sub-cultured every week with medium refresh every 3-4 days. After 3 months, total DNA of NSC-34 was isolated with QIAamp DNA mini kit (Qiagen, Hilden, Germany). $MT-CO_1$ and MT-ND1 were tested by PCR. PCR was performed in a total 25 μl volume including 41 of PCR Master mix (Thermofisher Scientific, Waltham, MA, USA), 0.5 μl of 100 μM forward and reverse primers and 200 ng DNA template. The primers used for amplification of MT-CO1 were 5'-CTAGCCGCAGGCATTACTATAC-3' (SEQ ID NO 1) and 5'-TGTCAAGGGATGAGTTGGATAAA-3' (SEQ ID NO 2). The primers for MT-ND1 were 5'-GCCGTAGCCCAAACAATTTC-3' (SEQ ID NO 3) and 5'-CGTAACGGAAGCGTGGATAA-3' (SEQ ID NO 4). Mouse β-actin (mACTB) was used as a control of genomic gene. The primers for mACTB amplification were 5'-CTGAGTCTCCCTTGGATCTTTG-3' (SEQ ID NO 5) and 5'-AGGGCAGGTGAAACTGTATG-3' (SEQ ID NO 6). The amplification procedure included initial DNA denaturing at 95° C. for 3 minutes, then 35 cycles of denaturing 30 seconds at 95° C., primer annealing 30 seconds at 50° C. and 60 seconds of extension at 72° C., and final extension of 10 minutes at 72° C. in a T100 Thermal Cycle (Bio-Rad, Hercules, Calif., USA). PCR products were run on a 2% agarose gel and imaged by ethidium bromide fluorescence.

Mitochondrial Transplantation to mtDNA-Depleted NSC-34 (NSC-34ρ⁰)

Mitochondria were isolated from mouse NSC-34 cells. The mitochondria (from 1×10⁶ cells) were co-cultured with 1×10⁵NSC-34 ρ⁰ cells (Mitochondria from 10 NSC-34 cells+1 NSC-34 ρ⁰ cell). Normal NSC-34 was used as control. After 24 hours of co-culture, the media containing the mitochondria were removed. Cells were washed twice, refilled with fresh complete DMEM, and continuously cultured. DNA and RNA of cells were isolated at 1, 3 and 6 days, respectively, after transplantation for PCR and real time PCR examination. For imaging of mitochondrial transplantation, mitochondria of NSC-34 cells and primary fibroblasts were labelled with MitoTracker Red, isolated and co-cultured with NSC-34 ρ⁰ cells for 24 hours (Mitochondria from 10 NSC-34 cells or fibroblasts+1 NSC-34 ρ⁰ cell). After removal of the media containing the labelled mitochondria, cells were observed under fluorescent microscope.

Real Time PCR (qPCR)

Quantitative real time polymerase chain reaction (qPCR) was used to measure mRNA levels of mitochondrial and glycolysis-associated genes. The following were examined: mitochondrial OXPHOS genes, MT-CO1 and MT-ND1, and glycolysis-associated genes HK2, SLC2A1 and LDHA which catalyzed the reduction of pyruvate by NADH to form lactate. All gene expression quantification was performed with TaqMan Gene Expression Assay, a proven 5' nuclease-based real-time PCR chemistry. Primers and probes (PrimeTime Mini qPCR assay) were synthesized by Integrated DNA Technologies (IDT, Coralville, Iowa) (Table 1, SEQ ID NOS: 7-24). β-actin (ACTB) was used as endogenous gene control to normalize PCRs for the amount of RNA added to the reverse transcription reactions. Probes contain at the 5' end the FAM (6-carboxy fluorescein) as a fluorescent reporter dye, and internal and at 3' end the ZEN™/Iowa Black FQ as fluorescent double quenchers. The qPCR reaction was performed with 7900HT real time PCR system (Applied Biosystems, Grand Island, N.Y.). Standard mode ran as 2 minutes at 50° C. and 10 minutes at 95° C., and 40 cycles (15 seconds at 95° C. and 1 minute at 60° C.). Target gene expression was determined by relative quantification which related signal of the target transcript in an experimented group to that of a control. Relative quantification was analyzed with the RQ Manager 1.2.1 software (Applied Biosystems, Grand Island, N.Y., USA).

Mitochondrial Transplantation to Mammary Adenocarcinoma 4T1 Cells in Mouse

The Institutional Animal Care and Use Committee (IACUC) protocol was submitted and approved by LSU School of Veterinary Medicine. Female mice were 16-18 grams (average 17.3 g) and 8 weeks old. 1×10⁵ mouse mammary adenocarcinoma 4T1 cells in 0.2 ml 0.9% NaCl was injected subcutaneously into each mouse. When tumor grew to 1 cm diameter, 0.2 ml of isolated mitochondria (5×10⁷ mitochondria) from 1.0×10⁶ EpH4-Ev cells were directly injected into tumor. The mitochondria of normal epithelial EpH4-Ev were pre-labelled with MitoTracker orange dye, isolated and stored in MRB on ice. After 24 hours, tumor was biopsied and smeared on glass slides. Tumor smearing slides were observed under fluorescent microscope to check whether the labeled mitochondria entered into 4T1 tumor cells. To examine inhibition of normal mitochondria to tumor cells, a mixture of 1×10⁵ 4T1 and mitochondria (5×10⁷ mitochondria) cells in 0.2 ml of MRB was injected subcutaneously into the dorsal cervical area of mouse (1 tumor 4T1 cell+ mitochondria from 10 EpH4-Ev cells). Control group mice were only injected with 1×10⁵ 4T1 cells in 0.2 ml of MRB per mouse. Control group and mitochondria-treated group contained 10 and 11 mice, respectively. At 18 days post-injection, mice were sacrificed and necropsied. Tumor mass and organs including lungs, liver, heart, spleen, and kidneys were removed and weighed. All tissues were fixed in 4% formalin solution for histological study.

Statistical Analysis

Student's t-test was used to test statistical significance. A p-value less than 0.05 was judged to be of statistical significance.

Results

Number, Protein Content and Viability of Isolated Mitochondria

Figure 2:
FIG. 2 is an image of viable mitochondria isolated from fibroblasts, according to an illustrative embodiment. The mitochondria maintain membrane potential gradient, actively concentrate JC-1 and form bright red fluorescent aggregates (J-aggregates).

The life span of the human primary fibroblasts was found to be approximately 80 days. The double time of growth is 40±6 hours. Mitochondria of fibroblasts were labeled with CellLight Mitochondria-GFP and the number of mitochondria per fibroblast was counted in 30 different fields using Cellsense software of the Olympus IX83 fluorescent microscope. There were 337±80 mitochondria (mean±standard deviation) per human fibroblast. FIG. 1 shows the GFP-labelled mitochondria of fibroblasts. Mitochondrial viability was assessed using mitochondrial fluorescent probes. It was found that the isolated mitochondria maintained membrane potential gradient, actively concentrated JC-1, and formed bright red fluorescent aggregates (J-aggregates). FIG. 2 shows the viable mitochondria isolated from fibroblasts. This finding suggests that the isolated mitochondria are viable and maintain electrochemical potential gradient. A total of $(1.43±0.33)×10^9$ mitochondria could be isolated from $1×10^7$ fibroblasts which have a total of $(3.37×80)×10^9$ mitochondria in cells. The mitochondrial isolation protocol can obtain 42.4% $[(1.41×10^9) (3.37×10^9)×100\%]$ of fibroblast mitochondria. Mitochondrial protein content is an alternative method to estimate mitochondrial number. The $(1.43±0.33)×10^9$ mitochondria that were isolated from $1×10^7$ fibroblasts have 190±45 µg protein content. Both the fibroblast number and mitochondrial protein content can be used to estimate the number of isolated mitochondria.

Fibroblast's Mitochondria do not Express HLA-I Antigen

Figure 3A:
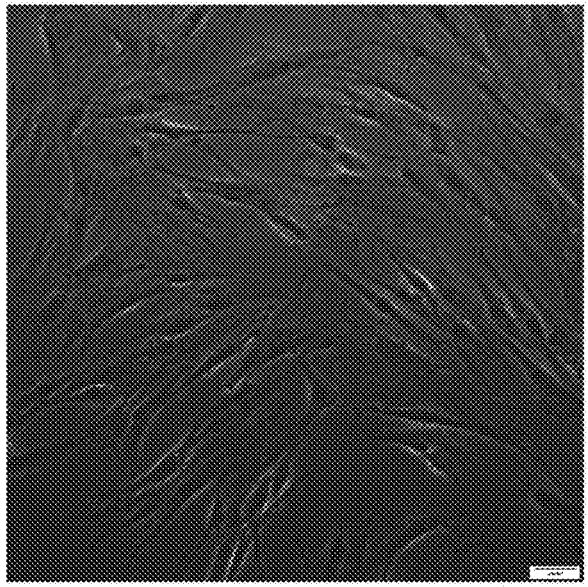
FIGS. 3A-D are images showing immune fluorescent staining of HLA-I antigen, according to an illustrative embodiment. There is green fluorescent staining on cell surface of fibroblasts (FIG. 3B) but no positive staining in isolated mitochondria (FIG. 3D).
Figure 3B:
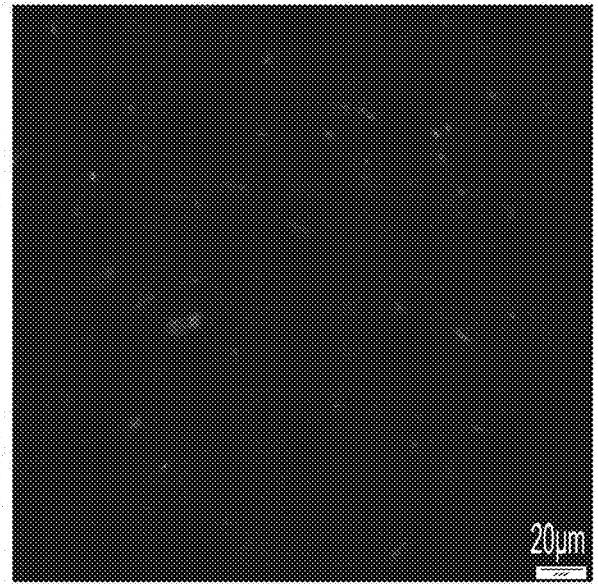
Figure 3C:
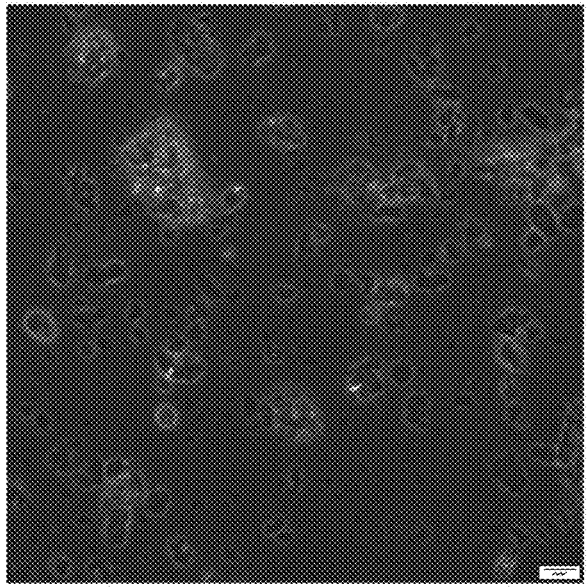
Figure 3D:
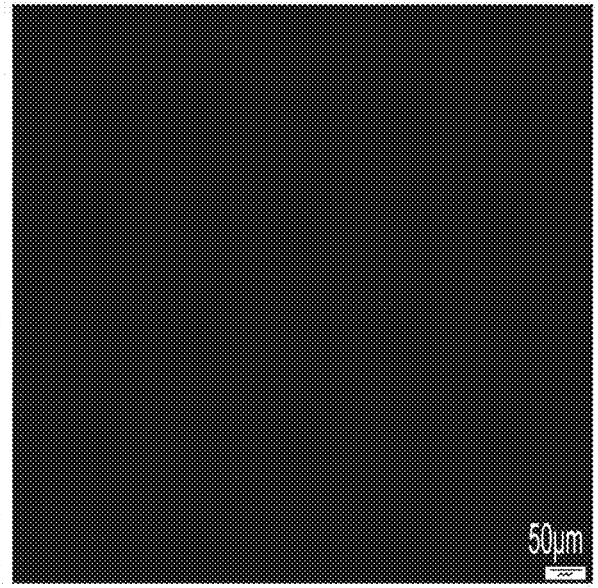

Green fluorescence is found on cell surface of human fibroblasts. The distribution of green fluorescence is uneven. The finding suggests HLA class I antigens mainly express on cell surface of human fibroblasts. The isolated mitochondria have no green fluorescent staining. These results suggest that mitochondria of human fibroblasts don't express HLA antigens and may be used for allogeneic mitochondrial transplantation without HLA antigen match. To illustrate, FIGS. 3A-D show immune fluorescent staining of HLA-I antigen. There is green fluorescent staining on cell surface of fibroblasts (FIG. 3B) but no positive staining in isolated mitochondria (FIG. 3D). FIG. 3A, FIG. 3C show phase contrast; FIG. 3B, FIG. 3D show fluorescence; FIG. 3A, FIG. 3B show fibroblasts; and FIG. 3C, FIG. 3D show isolated mitochondria from fibroblasts.

Mitochondria Transfer Between Human Fibroblasts and Mammary Adenocarcinoma MCF-7

Figure 4:
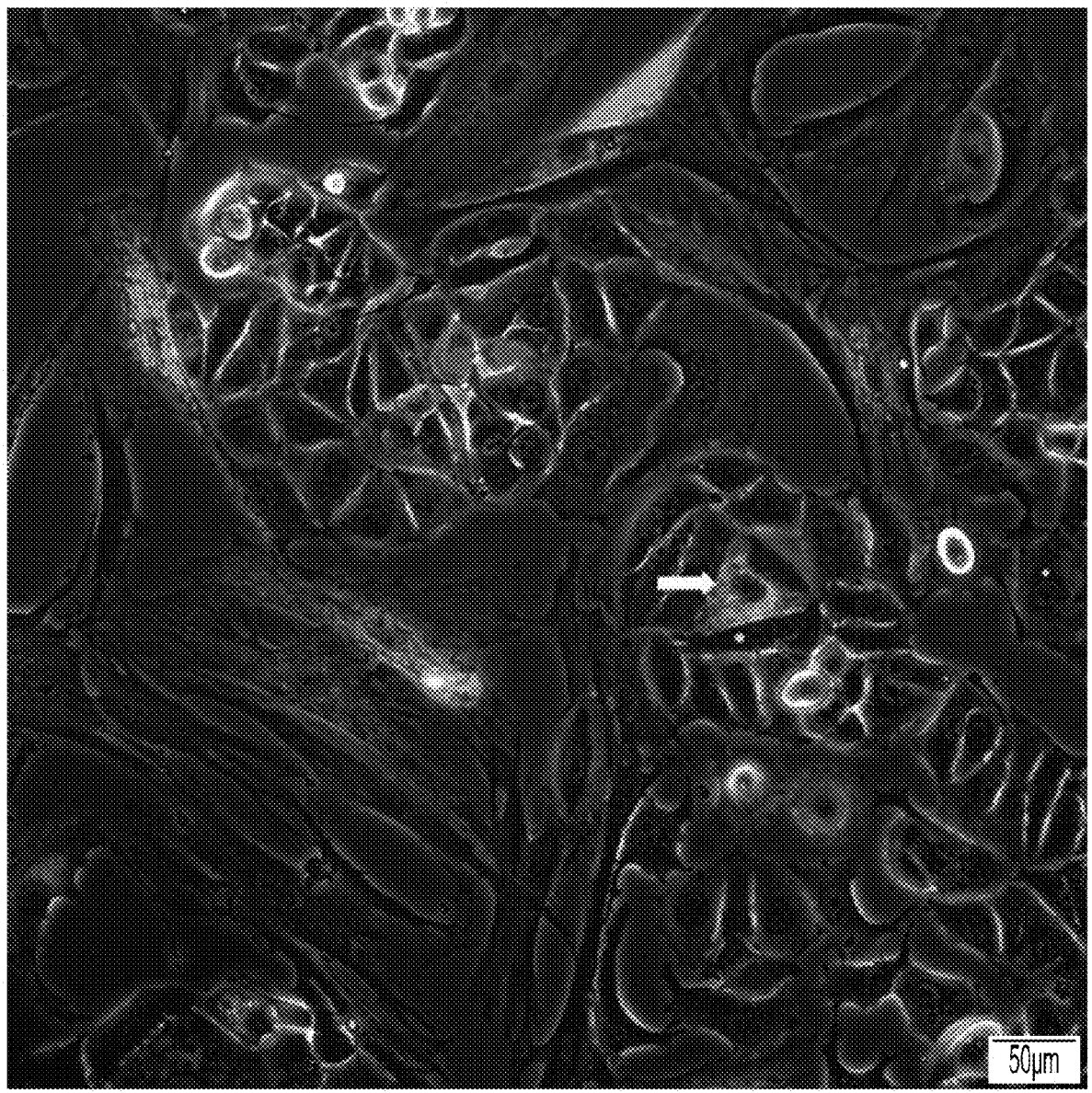
FIG. 4 is an image of fibroblasts that transfer mitochondria to MCF-7 cancer cells, according to an illustrative embodiment. The cell to which the arrow is pointing has mitochondria from both fibroblast and MCF-7. Thus, the mitochondria show an orange fluorescence.

CellLight Mitochondria-GFP-labelled fibroblasts were co-cultured with CellLight Mitochondria-RFP-labelled MCF-7 for 24 hours. Mitochondria moving between fibroblasts (green) and MCF-7 cells (red) resulted in orange fluorescence in some cells (see arrow in FIG. 4). FIG. 4 shows fibroblasts transferred mitochondria to MCF-7 cancer cells. The cell, indicated by the arrow, has mitochondria from both fibroblast and MCF-7. Thus, the mitochondria show orange fluorescence.

Normal Mitochondria Transplant to NSC-34 $\rho^0$ Cells

Figure 5:
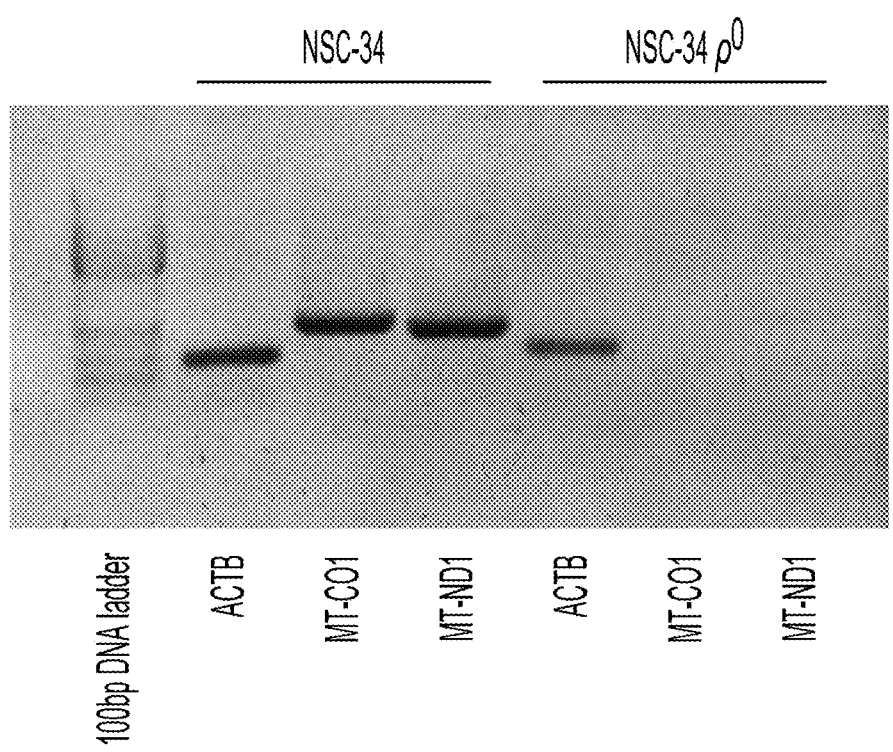
FIG. 5 is an image that shows NSC-34 $\rho^0$ cells lost mitochondrial DNA, according to an illustrative embodiment. No MT-CO1 and MT-ND1 gene is amplified in NSC-34 $\rho^0$ cells. Genomic gene ACTB is same as parent NSC-34 cells.
Figures 6A, 6B:
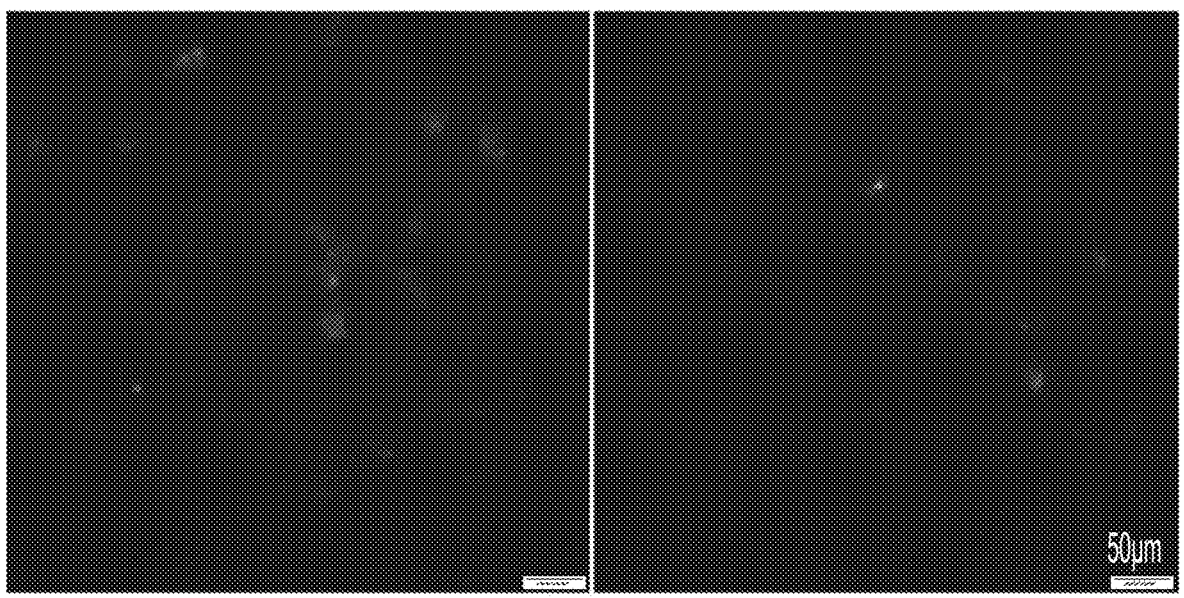
FIGS. 6A and 6B are a series of images that show mitochondria of NSC-34 and primary fibroblast transplant to NSC-34 $\rho^0$ cells, according to an illustrative embodiment. The mitochondria of NSC-34 and fibroblasts were labelled with MitoTracker red, isolated, and co-cultured with NSC-34 $\rho^0$ cells for 24 hours.

After treatment of NSC-34 with 2 µg/ml EtBr for 3 months, PCR showed there was no amplification of mitochondrial genes MT-CO1 and MT-ND1. The treatment had no effect on genomic gene ACTB amplification. For example, FIG. 5 shows NSC-34 $\rho^0$ cells lost mitochondrial DNA. No MT-CO1 and MT-ND1 gene was amplified in the NSC-34 $\rho^0$ cells. Genomic gene ACTB is the same as parent NSC-34 cells. The results suggest long term EtBr-treatment depleted mtDNA of NSC-34 cells. NSC-34 $\rho^0$ cells grow much more slowly than parent NSC-34. The growth of NSC-34 $\rho^0$ cells is approximately 10% of parent NSC-34. Isolated MitoTracker red-labelled mitochondria from NSC-34 cells or primary fibroblasts were co-cultured with NSC-34 $\rho^0$ cells. At 24 hours post-culture, mitochondria with red fluorescence were observed in NSC-34 $\rho^0$ cells (see FIG. 6A, FIG. 6B). FIGS. 6A-B show mitochondria of NSC-34 and primary fibroblast transplant to NSC-34 $\rho^0$ cells. The mitochondria of NSC-34 and fibroblasts were labelled with MitoTracker red, isolated, and co-cultured with NSC-34 $\rho^0$ cells for 24 hours. FIG. 6A is transplanted with NSC-34 mitochondria; FIG. 6B is transplanted with fibroblast mitochondria. These results suggest that isolated autologous and xenogeneic mitochondria transplant to the defective NSC-34 $\rho^0$ cells.

Figure 7:
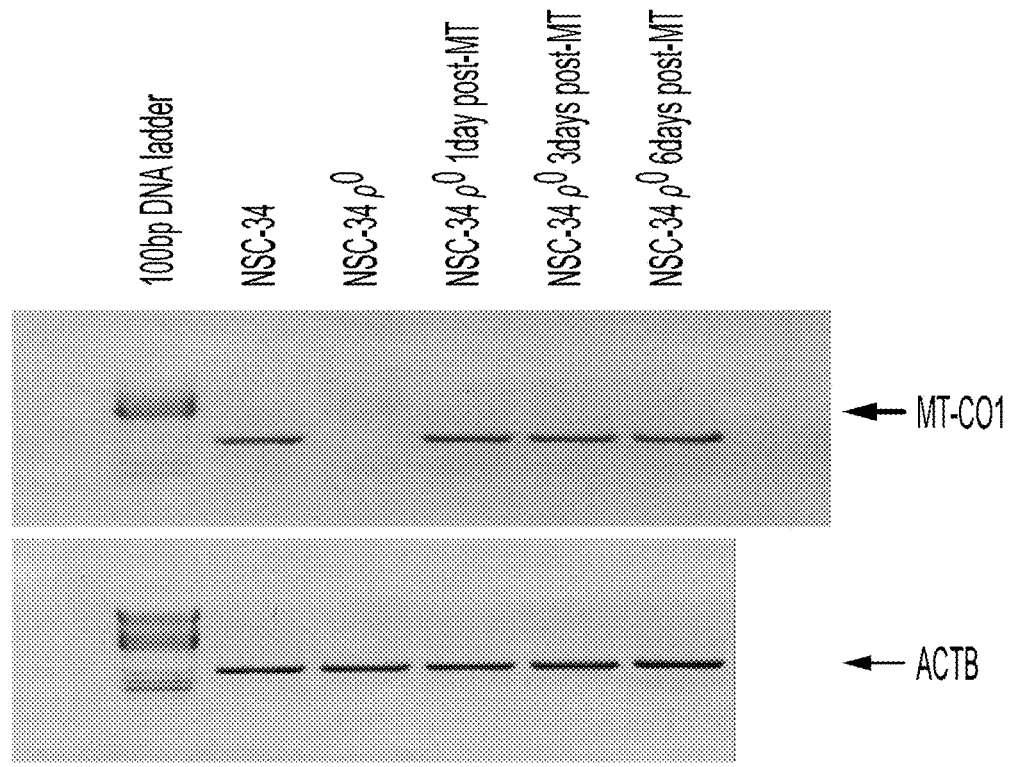
FIG. 7 is an image that shows autologous NSC-34 mitochondria replenish mitochondrial DNA of NSC-34 $\rho^0$ cells, according to an illustrative embodiment. There are bands of MT-CO1 amplification at 1, 3 and 6 days post-mitochondrial transplantation (MT).
Figure 8:
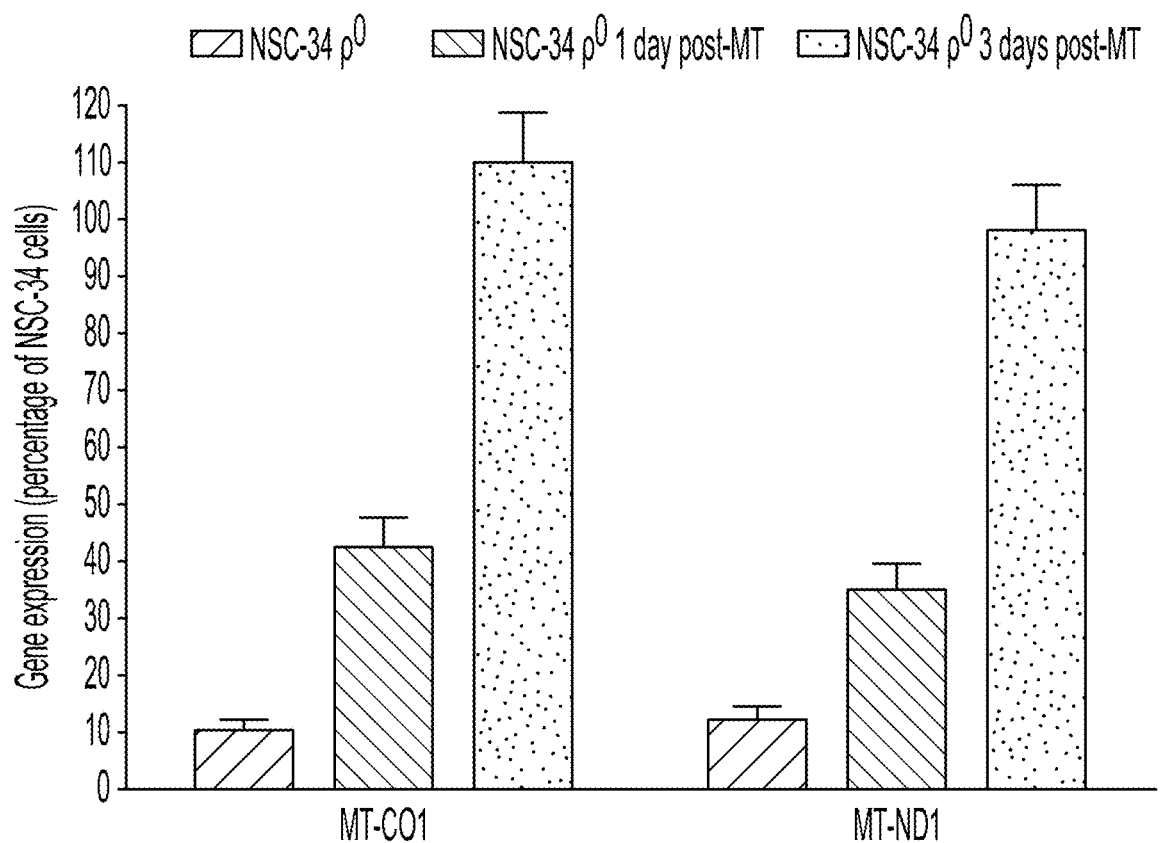
FIG. 8 is an image that shows autologous NSC-34 mitochondria restore MT-CO1 and MT-ND1 gene expression of NSC-34 $\rho^0$ cells, according to an illustrative embodiment. NSC-34 $\rho^0$ cells were co-cultured with isolated mitochondria from NSC-34 cells (1 NSC-34 $\rho^0$ cell+mitochondria from 10 NSC-34 cells). Gene expression is measured by qPCR.

Mitochondria of NSC-34 Replenish mtDNA and Rescue Aerobic Respiration of NSC-34 $\rho^0$ Cells After co-culturing of NSC-34 $\rho^0$ cells with the isolated NSC-34 mitochondria for 24 hours, PCR shows that MT-CO1 DNA genes are amplified in NSC-34 $\rho^0$ cells. Moreover, MT-CO1 remains following amplification at 3 and 6 days post-mitochondrial transplantation (FIG. 7). FIG. 7 shows autologous NSC-34 mitochondria replenish mitochondrial DNA of NSC-34 $\rho^0$ cells. There are bands of MT-CO1 amplification evident at 1, 3 and 6 days post-mitochondrial transplantation (MT). Amplification of genomic gene ACTB is not changed by mitochondrial transplantation. Levels of gene expression are calculated via the following formula: (gene expression of NSC-34 $\rho^0$÷gene expression of NSC-34 cells)×100%. qPCR shows that NSC-34 $\rho^0$ cells have very low levels of mRNA expression of mitochondrial genes MT-CO1 and MT-ND1 (approximately 10% of parent NSC-34 cells), but regain mRNA expression to the levels of normal NSC-34 at 3 days post-mitochondrial transplantation (FIG. 8). FIG. 8 shows that autologous NSC-34 mitochondria restore MT-CO1 and MT-ND1 gene expression of NSC-34 $\rho^0$ cells. NSC-34 $\rho^0$ cells were co-cultured with isolated mitochondria from NSC-34 cells (1 NSC-34 $\rho^0$ cell+mitochondria from 10 NSC-34 cells). Gene expression was measured by qPCR. The expression of glycolytic genes, HK2, LDHA and SLC2A1, is upregulated in NSC-34 $\rho^0$ cells. These suggest NSC-34 $\rho^0$ cells with defective mitochondria increase aerobic glycolysis to produce cell energy ATP. Mitochondrial transplantation downregulates expression of the glycolysis-related genes.

Figure 9:
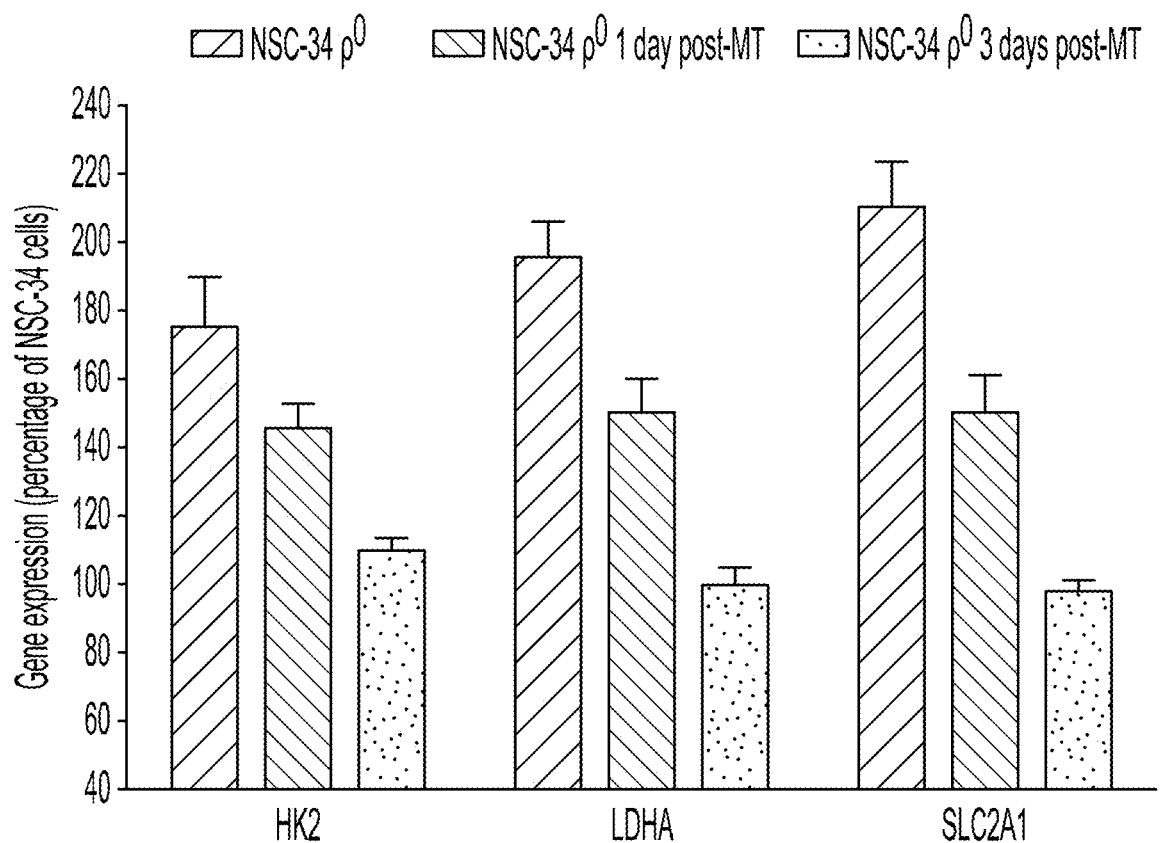
FIG. 9 is an image that shows autologous NSC-34 mitochondria reverse the expression of glycolytic genes of NSC-34 $\rho^0$ cells, according to an illustrative embodiment. NSC-34 $\rho^0$ cells were co-cultured with isolated mitochondria from NSC-34 cells (1 NSC-34 $\rho^0$ cell+mitochondria from 10 NSC-34 cells). Gene expression is measured by qPCR.

The levels of HK2, LDHA and SLC2A1 gene expression return to normal at 3 days post-transplantation of NSC 34 mitochondria (FIG. 9). FIG. 9 shows autologous NSC-34 mitochondria reverse the expression of glycolytic genes of NSC-34 $\rho^0$ cells. NSC-34 $\rho^0$ cells were co-cultured with isolated mitochondria from NSC-34 cells (1 NSC-34 $\rho 0$ cell+mitochondria from 10 NSC-34 cells). Gene expression was measured by qPCR. These results suggest that the isolated NSC-34 mitochondria can effectively replenish mitochondrial DNA and rescue aerobic respiration of NSC-34 $\rho^0$ cells. In this study, 10 NSC-34 cells' mitochondria can rescue 1 NSC-34 $\rho^0$ cell with defective mitochondria.

Thus, the experiments above demonstrate xenogeneic mitochondria from human fibroblasts successfully enter NSC-34 $\rho^0$ cells (see, e.g., FIG. 6B, and description above).

Mitochondrial Transplantation in Mouse 4T1 Tumor Model

Figure 10:
FIG. 10 is an image that demonstrates MitoTracker orange-labelled mitochondria of EpH4-Ev successfully transplant to 4T1 cells grown in mice, according to an illustrative embodiment. Orange fluorescence was observed in 4T1 cells on tumor smearing slides at 24 hours post-injection of mitochondria.

At 24 hours post-injection of MitoTracker orange-labelled mitochondria of normal EpH4-Ev cells into tumor mass, orange fluorescence was observed in 4T1 cells (FIG. 10). FIG. 10 shows MitoTracker orange-labelled mitochondria of EpH4-Ev successfully transplant to 4T1 cells grown in mice. Orange fluorescence was observed in 4T1 cells on tumor smearing slides at 24 hours post-injection of mitochondria. This result suggests that the mitochondria of EpH4-Ev cells successfully transplant into tumor 4T1 cells. At 18 days of experiment, mice were necropsied. Tumor weight in the group that received normal EpH4-Ev mitochondria is not different from tumor weight of the control group ($p>0.05$). Gross examination shows all mice have lung metastases in both groups. However, lung weight of the group that received mitochondria is less than that of the control group even though the difference is not quite significant ($p=0.06$) (see Table 2 in Discussion subsection below). These results suggest that exogeneous normal mitochondria might decrease metastatic burden in lungs.

Subcutaneous injection of mitochondria [$5\times10^7$ mitochondria (6.6 μg protein) per mouse] and MRB (0.2 ml/mouse) didn't cause any side reaction in mice. The doses in mice can be converted to doses of human based on body surface area as the formula: dose of human per kilogram (kg) body weight=mouse dose per kg$\times0.081$. In this study, mouse averaged weight is 17.3 g. The doses of mice are 0.38 mg/kg [0.0066 mg (mitochondrial protein)$\div0.0173$ kg mouse weight], or $2.89\times10^9$ mitochondria/kg ($5\times10^7$ mitochondria$\div0.0173$ kg mouse weight). The equivalent of human doses will be: 0.031 mg/kg (0.38 mg/kg in mice$\times0.081$) in protein or $2.34\times10^8$ mitochondria/kg ($2.89\times10^9$ in mice$\times 0.081$). These doses can be used as starting dose for a clinical trial. Other doses may be used as well. Subcutaneous injection of 0.2 ml of MRB is safe for mice. Conversion of the MRB volume to human will be 2-5 ml intramuscular injection per site or <250 ml intravenous injection.

DISCUSSION

The exact etiologies of most neurodegenerative diseases (NDs) remain unclear. Current effective treatment for NDs is limited. NDs are often associated with mitochondrial dysfunction. Thus, targeting to mitochondria-related pathogenesis has increased attention to NDs treatment. Traditional drugs or gene targeting agents do not easily (or do not) arrive at specific sub-compartments of mitochondria. Moreover, the diverse nature of mitochondrial mutations among patients may make it impossible to develop one drug to cure one disease. In recent years, mitochondrial transplantation has shed a new light of therapeutic intervention that benefits neuronal survival and regeneration for neurodegenerative diseases, stroke, and CNS injury. As presented herein, it is found that exogenous healthy mitochondria transplant to defective neurons and promote neuronal viability, activity and neurite re-growth. In this study, mtDNA-depleted motor neuron NSC-34 (NSC-34$\rho^0$) cells grow much slower than parent NSC-34 cells. NSC-34 $\rho^0$ cells increase aerobic glycolysis, a less efficient pathway to make ATP than OXPHOS (see FIG. 9). NSC-34 $\rho^0$ cells can be a mitochondrial defective model of motor neuron. Motor neurons in brain and spinal cord have defects and stop working properly in ALS patients. NSC-34 $\rho^0$ cells are a useful tool for mitochondrial pathogenesis research of ALS. Transplantation of NSC-34 mitochondria replenishes mtDNA of NSC-34 $\rho^0$ cells confirmed by PCR (FIGS. 7-8). After mitochondrial transplantation, the expression of glycolytic genes HK2, LDHA and SLC2A1 are decreased at 1 day and to the normal levels of NSC-34 cells at 3 days (FIG. 9).

A registered study for mitochondrial transplantation on ClinicalTrials.gov "Transplantation of Autologously Derived Mitochondria Following Ischemia" (https://clinicaltrials.gov/ct2/show/NCT02851758) described that human autologous mitochondria of skeletal muscle will be injected to ischemic cardiac muscle. Like cardiac muscle, skeletal muscle is striated. In addition, skeletal muscle is plentiful in humans. Thus, skeletal muscle is a reasonable mitochondrial donor tissue for mitochondrial transplantation following cardiac ischemia. However, it is difficult to find allogeneic or autologous neurons as mitochondrial donor because nerve systems are limited in self-repair and regeneration. In the work described herein, human fibroblasts were selected as mitochondrial donors in mitochondrial transplantation for human NDs for following reasons: 1) Fibroblasts have abundant tissue sources and are capable of regeneration in human; 2) Fibroblasts often exchange mitochondria with other cells including neurons; 3) Fibroblasts share many characteristics with mesenchymal stromal/stem cells (MSCs). MSCs cellular therapy has been used in trials for inflammatory, immune-mediated, and degenerative diseases, attributed to their immunomodulatory, immunosuppressive and regenerative potentials; and 4) Human fibroblasts can be induced to functional neurons. In the studies presented herein, it was found that human primary fibroblasts are readily isolated and quickly expanded. Mitochondria are dynamic cell organelles with continuous fission and fusion. However, cells have a relatively stable number of mitochondria in normal physiological situations. The number of mitochondria in a cell can vary widely by organ, tissue, and cell type. For instance, red blood cells have no mitochondria, whereas liver cells can have more than 2000 each. The human fibroblasts have abundant mitochondria (averaged 337 mitochondria per fibroblasts). It was found in the work described herein that human fibroblasts transfer mitochondria to human mammary adenocarcinoma cell line MCF-7 (see FIG. 4). Mitochondrial transfer between fibroblasts and cancer might benefit cancer growth. However, fibroblast mitochondrial transfer with normal cells may rescue aerobic respiration of injured cells and benefit tissue repair and regeneration. The protocol of mitochondrial isolation described herein yielded 42.4% of intracellular mitochondria of fibroblasts. Fibroblast number can be used as a fast method to estimate mitochondrial number during mitochondrial transplantation trial because of the short life of isolated mitochondria (less than a few hours on ice). From $1\times10^7$ fibroblasts, the final number of the isolated mitochondria are $1.43\times10^9$ ($1\times10^7\times337\times42.4\%=1.43\times10^9$). Mitochondrial protein content is an alternative way to determine mitochondrial number, but the procedure often takes a few hours. Thus, mitochondria protein content is less practical than cell number to estimate mitochondrial number in mitochondrial transplantation trial. The isolated mitochondria maintain membrane potential gradient. Mitochondrial membrane potential is generated by proton pump (Complex I, III and IV) and serves as an intermediate form of energy storage which is used by ATP synthase to make ATP. Membrane potential is also a factor determining viability of mitochondria and a driving force for transport of charged compounds some of which are essential for mitochondrial viability. Loss of mitochondrial membrane potential will induce mitophagy to eliminate the damaged mitochondria. Thus, mitochondrial membrane potential is a marker for viability of isolated mitochondria. Mitochondrial membrane potential can be determined by mitochondrial fluorescent probes such as JC-1, MitoTracker dyes, Tetramethylrhodamine ethyl (TMRE) or methyl (TMRM) ester. Isolated mitochondrial viability can be rapidly and readily determined by using the mitochondrial fluorescent probes. The isolated fibroblast's mitochondria successfully transplant to defective mouse motor neuron NSC-34 $\rho^0$ cells (FIG. 6B). This shows xenogeneic mitochondria can transplant to recipient cells from different species. Overall, it is found that human primary fibroblasts are a viable and potentially ideal mitochondrial donor for mitochondrial transplantation for NDs.

Allogeneic tissue donors require an HLA typing match. The human leukocyte antigen (HLA) system or complex is a group of related proteins that are encoded by the major histocompatibility complex (MHC) gene complex in humans. HLA I molecules are one of two primary classes of MHC molecules on cell surface of all nucleated cells, and include HLA-A, HLA-B, and HLA-C. HLA II is found only on professional antigen-presenting cells such as dendritic cells and B cells. The immune system uses the HLAs to differentiate self cells from non-self cells. Fibroblasts may express low level of HLA I antigen because of similarity of fibroblasts and MSCs. The results described herein show primary fibroblasts express HLA-I antigen on cell surface, but the isolated mitochondria from fibroblasts don't express any HLA-I antigen (FIGS. 3A-D). These results suggest allogeneic mitochondria exhibit low or no immunogenicity and need no HLA tying match in mitochondrial transplantation. It is possible that fibroblast mitochondria may be used as a "Off-the-Shelf" product for biotherapy.

Furthermore, mitochondrial transplantation may have potential for cancer therapy. It is seen that mitochondria isolated from normal mammary epithelial MCF-12A transplant to human breast carcinoma cell lines, downregulate gene expression of glycolytic enzymes and increase cancer drug sensitivity. In the work described herein, it is found that normal mitochondria successfully enter the tumor 4T1 cells in mice at 24 hours after mitochondrial injection in tumor mass (FIG. 10). In other groups of mice, normal mitochondria (mitochondria from 10 EpH4-Ev cells+1 tumor 4T1 cell) fail to inhibit tumor growth. Normal mitochondria decrease lung weight but the difference is not quite significant (p=0.06), compared to the control group. Inhibitory effect of normal mitochondria on tumor cells may depend on dosage of mitochondria. It was found that subcutaneous injection of 0.2 ml mitochondria and MRB is safe for mice. The mitochondria number and MRB volume in mice can be converted to human dose as an estimation of starting dose for clinical trial.

It is found herein that human primary fibroblasts are a suitable mitochondrial donor for mitochondrial transplantation for treatment of human neurodegenerative diseases. Furthermore, it is found that mitochondrial transplantation can replenish mtDNA and rescue aerobic respiration of cells with defective mitochondria.

TABLE 1

List of primer and probe sequences for qPCR

| Gene | Pair of primers (FWD and REV) | Probe |
| --- | --- | --- |
| ACTB | GAGGTATCCTGACCCTGAAGTA: CACACGCAGCTCATTGTAGA | TGGCATTGTTACCAACTGGGACGA |
| MT-CO1 | ACCACCATCATTTCTCCTTCTC; CTCCTGCATGGGCTAGATTT | AAGCAGGAGCAGGAACAGGATGAA |
| MT-ND1 | CCATTTGCAGACGCCATAAA: GAGTGATAGGGTAGGTGCAATAAAGAACCAATACGCCCTTTAACAACCTCT | |
| HK2 | TCAAAGAGAACAAGGGCGAG; AGGAAGCGGACATCACAATC | AGAAACATCCCCATTTTGCCAAGCG |
| SLC2A1 | GATTGGTTCCTTCTCTGTCGG; CCCAGGATCAGCATCTCAAAG | TTATGGGCTTCTCCAAACTGGGCA |
| LDHA | GCTCCCCAGAACAAGATTACAG: TCGCCCTTGAGTTTGTCTTC | AGCTCATCCGCCAAGTCCTTCATT |

Table 1 above discloses SEQ ID NOS 7-24, respectively, in order of appearance.

TABLE 2

Weights of tumor and lungs in 4T1 mammary adenocarcinoma bearing mice treated subcutaneously with mitochondria of EpH4-Ev mammary epithelia.

| | Control | Transplanted with mitochondria | p$^\&$ |
| --- | --- | --- | --- |
| Tumor weight (g) | 1.0 ± 0.27 (11)* | 1.1 ± 0.27 (10) | 0.48 |
| Lung weight (g) | 0.45 ± 0.10 (11) | 0.37 ± 0.10 (10) | 0.06 |

*mean ± standard deviation (number of mice)
$^\&$Student's t-test, less than 0.05 was judged to be of statistical significance.

Experimental Example II

Fibroblasts were derived from a young male adult skin tissue. The donor is healthy and has no virus infections. The donor signed a release form regarding use of his tissue. 250 mg of surgically removed skin tissue was minced with sterile scalpels and was digested for 5 hours at 37° C. in alpha-MEM containing 6.25% fetal calf serum (GIBCO Invitrogen, Carlsbad, Calif., USA), 0.56% collagenase (Worthington Biomedical, Lakewood, N.J.) and 0.004% DNase (Sigma Aldrich, St. Louis, Mo.). Then, the cell mixture was centrifuged for 5 minutes at 400 g. The supernatant was removed. The cell pellet was re-suspended in completed alpha-MEM supplemented with 10% fetal calf serum and 1 mM glutamine (GIBCO Invitrogen, Carlsbad, Calif., USA), and incubated at 37° C. with 5% $CO_2$. After large fibroblast colonies appeared, they were removed with a sterile cell scraper from the flask and transferred to new flask containing fresh culture medium (same composition as above). When fibroblast grew to 80% full in flask, they were digested with 0.05% trypsin and 0.53 mM EDTA. Cells were grown in the media without supplement of antibiotics such as gentamicin, penicillin and streptomycin, etc. A large number of primary fibroblasts were frozen and stored in liquid nitrogen for future use. Antibiotics in culture media have toxicity to mitochondria of mammalian cells. Therefore, for MOT, human fibroblasts were cultured in antibiotic-free completed alpha-MEM supplemented with 10% fetal calf serum and 1 mM glutamine at 37° C. with 5% $CO_2$.

Mitochondrial Isolation Buffer and Storing Buffer

The mitochondrial isolation buffer in this experimental example consists of 300 mM sucrose, 10 mM K-HEPES, 1 mM K-EGTA, 0.1% BSA and 0.25 mM PMFS (Sigma Aldrich, St Louis, Mo., USA). The osmolarity of the buffer is 325 mOsm. The concentration of potassium ion is 11 mM. Bovine serum albumin (BSA) is a membrane stabilizer, oxygen radical scavenger, and binds $Ca2^+$ and free fatty acids. Phenylmethylsulfonyl fluoride (PMFS), also called phenylmethane sulfonyl fluoride, is a serine protease inhibitor used in the preparation of cell lysates. Lysosomes are organelles that contain digestive enzymes which digest excess or worn out organelles. During the procedure of cell homogenization, some lysosomes may be damaged and release the digestive enzymes to the cell lysate. In order to prevent the damage of mitochondria from the digestive enzymes, we include PMFS in the isolation buffer.

The mitochondrial storing buffer in this experimental consists of 240 mM sucrose, 2 mM $KH_2PO_4$, 3 mM $MgCl_2$, 10 mM K-HEPES, 20 mM Taurine, 1 mM K-EGTA, 0.1% BSA and 15 mM K-lactobionate (Sigma Aldrich, St Louis, Mo., USA). Taurine acts as an antioxidant that scavenges free radical species generated by mitochondria, and is also involved to membrane stabilization, osmoregulation and ion channel regulation. Lactobionate has cytoprotective property and prevents mitochondrial swelling. Lactobionate also binds to calcium ion with high affinity and acts as a calcium chelator. The osmolarity of the mitochondrial storing buffer is 325 mOsm. The buffer contains 28 mM potassium ion. The buffers are sterilized by filtering through 0.22 µm filter and aliquoted to small vials and stored at −80° C.

In the clinical use discussed below, the fibroblast mitochondria in the storing buffer is administered intramuscularly and intravenously to human patients. High potassium ion concentrations are dangerous for injection to humans (e.g., 91 mM potassium ion concentration from buffer B2 (PLOS One https://doi.org/10.1371/journal.pone.0187523). In this experiment, a reduced concentration of all $K^+$ salts was used (2 mM $KH_2PO_4$, 10 mM K-HEPES, and 15 mM K-lactobionate). The final concentration of $K^+$ in the storing buffer solution used in the experiment is 28 mEq, which is similar to clinical intravenous solution with potassium chloride (20 mEq and 40 mEq). To keep the osmolarity similar, the concentration of sucrose was increased.

Mitochondrial Isolation

Use of cooling and rapid isolation is observed to be important, in preferred embodiments. All materials and reagents of mitochondrial isolation are pre-chilled on ice. All steps are performed at 0° C.-4° C. The brief procedure is as following: Fibroblasts are digested from flasks and pelleted by centrifugation. The fibroblast pellet is re-suspended in the mitochondrial isolation buffer and transferred to 2 ml sterile tubes with 1.0 mm beads. The bead-tubes are shaken for 2 minutes at 4000 rpm to homogenize the fibroblasts. The cell homogenate is poured over a 40 µm cell strainer, filtered into a 50 ml collection tube on ice, washed with 5 ml mitochondrial isolation buffer, and the process is repeated once. The homogenate is added onto a 10 µm cell strainer and filtered into 50 ml collection tubes on ice. The homogenate is centrifuged at 9000 g for 10 minutes at 4° C. The mitochondrial pellet is re-suspended in the mitochondrial storing buffer, stored on ice or used immediately.

Immunofluorescent Staining of HLA Class I in Human Fibroblasts and Mitochondria

Human leukocyte antigen (HLA) complex includes Class I (HLA-A, B, C) and Class II (HLA-DPA1, DPB1, DQA1, DQB1, DRA, and DRB1). HLA Class I antigens are present on the surface of almost all cells. HLA Class II antigens are present almost exclusively on the surface of certain immune system cells. Mismatch of HLA antigens between donors and recipients often results in rejection of cells and organs after cell therapy and organ transplantation. For the staining process 20,000 fibroblasts are cultured on 35 mm glass-bottom dishes overnight. Mitochondria of fibroblasts are stained by MitoTracker Red (Molecular Probes, Eugene, Oreg.). MitoTracker Red labels mitochondria within live cells with its accumulation dependent on mitochondrial membrane potential. MitoTracker is chemically reactive, linking to thiol groups in the mitochondria. The dye becomes permanently bound to the mitochondria, and thus remains after the cell dies or is fixed. The cells are fixed by 4% paraformaldehyde solution for 15 minutes at room temperature and washed by phosphate buffer solution (PBS). The cells are incubated with protein blocker for 1 hour at room temperature, washed 3 times with PBS, and incubated by rabbit anti-human HLA-ABC polyclonal antibody (Invitrogen, Carlsbad, Calif.) at 4° C. overnight. The cells in a blank control dish are incubated with PBS without HLA antibody. The dishes are washed with PBS 4 times and incubated with goat anti-rabbit IgG-Alexa 488 for 1 hour at room temperature, and further washed 4 times again. The cells are covered by 0.4 ml PBS and fluorescence is observed under Olympus IX83 fluorescent microscope (Tokyo, Japan). In addition, isolated mitochondria are fixed and incubated with antibodies as fibroblasts and immunofluorescent staining is observed.

Viability of Isolated Mitochondria

In order to determine viability of mitochondria isolated from human fibroblasts, a technique involving using 5,5,6,6'-tetrachloro-1,1',3,3' tetraethylbenzimidazoylcarbocyanine iodide (JC-1) dye (Sigma Aldrich, St Louis, Mo., USA) is used to detect mitochondrial membrane potential ($\Delta\Psi_M$). For cells with a normal $\Delta\Psi_M$, the JC-1 dye enters and accumulates in the energized and negatively charged mitochondria and spontaneously forms red fluorescent J-aggregates. By contrast, in unhealthy or apoptotic cells the JC-1 dye also enters the mitochondria but to a lesser degree since the inside of the mitochondria is less negative because of increased membrane permeability and leading to loss of electrochemical potential. Under this condition, JC-1 does not reach a sufficient concentration to trigger the formation of J aggregates thus retaining its original green fluorescence. JC-1 can be used to assess the ATM both in intact isolated mitochondria and tissues. Fibroblasts are stained by JC-1 (Sigma Aldrich, St Louis, Mo.). The JC-1-stained mitochondria are isolated by the above protocol. Fluorescence of the isolated mitochondria are observed under fluorescent microscopy. The red fluorescence suggests that the isolated mitochondria maintain membrane electrochemical potential and are viable.

Mitochondrial Organelle Transplantation (MOT) in Mouse Neural Motor Cell Line NSC-34

NSC-34 is a hybrid cell line, produced by fusion of motor neuron enriched, embryonic mouse spinal cord cells with mouse neuroblastoma (Cellutions Biosystems Inc., Burlington, Ontario, L7L 5R2, Canada). NSC-34 cells are cultured in complete DMEM medium containing 10% fetal bovine serum. Human fibroblast mitochondria are labeled with MitoTracker Red, isolated, and co-cultured with NSC-34 cells for 12 hours at 37° C. with 5% $CO_2$. The culture media are aspirated. The cells are washed with pre-warmed DMEM for 3 times and covered by 0.5 ml fresh DMEM medium. Fluorescence of NSC-34 cells is observed under Olympus IX83 fluorescent microscope (Tokyo, Japan). In addition, NSC-34 cells are cultured with DMEM medium containing 2,000 ng/ml ethidium bromide (EtBr). EtBr intercalates double-stranded DNA (i.e. inserts itself between the strands), deforming DNA and affect DNA biological processes including DNA replication and transcription. EtBr will cause mitochondrial DNA defects and eventually deplete mitochondrial DNA of NSC-34 cells. MOT of fibroblast mitochondria are tested in sick EtBr-treated NSC-34 cells as well as healthy NSC-34.

Preparation of MOT in Amyotrophic Lateral Sclerosis (ALS)

The mitochondria were isolated from 80-100×10$^6$ human fibroblasts. The mitochondria were re-suspended in 11 ml of the mitochondrial storing buffer. 4 mg of chimeric mitochondrion penetrating peptides was dissolved in 2 ml of the mitochondrial storing buffer and sterilized by filtering via 0.22 μm filter. The peptide consisted of the leader peptide of mitochondrial aldehyde dehydrogenase (ALDH2) with arginine-rich peptide. The amino acid sequence of the peptide was MLRAAARFGPRLGRRLLSARKKRRQRRR. (SEQ ID NO 25). The leader peptide can bind to mitochondrial outer membrane via protein translocase outer membrane (Tom) and the arginine-rich sequence can insert into the cell membrane. Thus, the chimeric peptide may increase the potential of exogenous mitochondria to enter into cells. The peptide solution was added into the 11 ml of fibroblast mitochondria and incubated for 30 minutes on ice. The mitochondria was drawn into eight 1 ml and one 5 ml syringes. The syringes were placed on the ice and used for intramuscular and intravenous injection in 30 minutes.

Results

Figure 11:
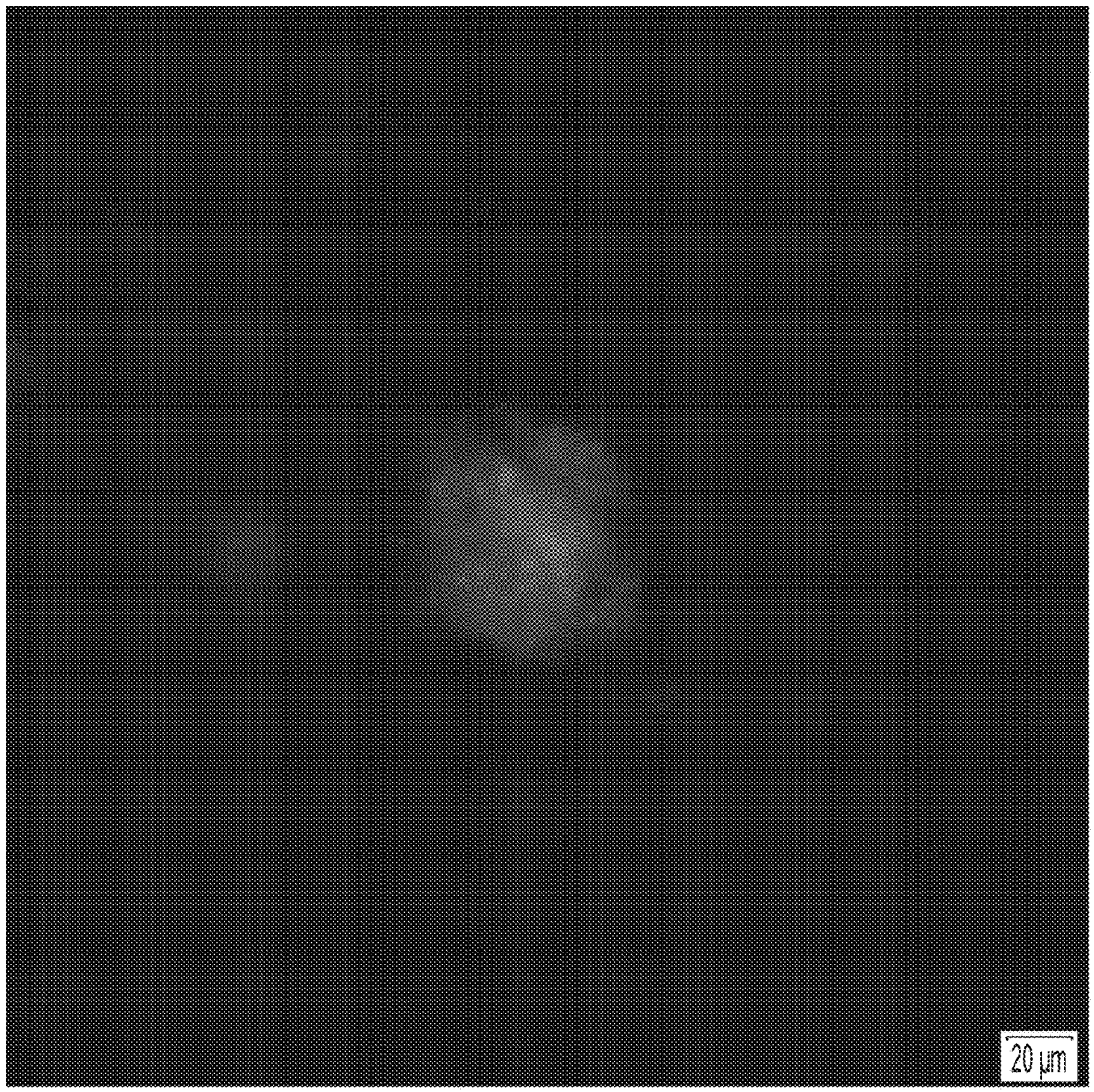
FIG. 11 is an image in which the isolated mitochondria show red fluorescence (J-aggregates) and retain membrane electrochemical potential, according to an illustrative embodiment. Mitochondria in fibroblasts are labeled by JC-1 and isolated, re-suspended in the mitochondrial storing buffer.

The Isolated Mitochondria Maintain Membrane Electrochemical Potential and Viability The isolated mitochondria can concentrate JC-1 dye and form J aggregates. Thus, red fluorescence is found in the mitochondrial colonies (FIG. 11). The finding confirms that the protocol of the mitochondrial isolation and storage can purify and maintain viable mitochondria for the following MOT in cell lines and patients.

Human Mitochondria do not Express HLA Antigens

Figure 12A:
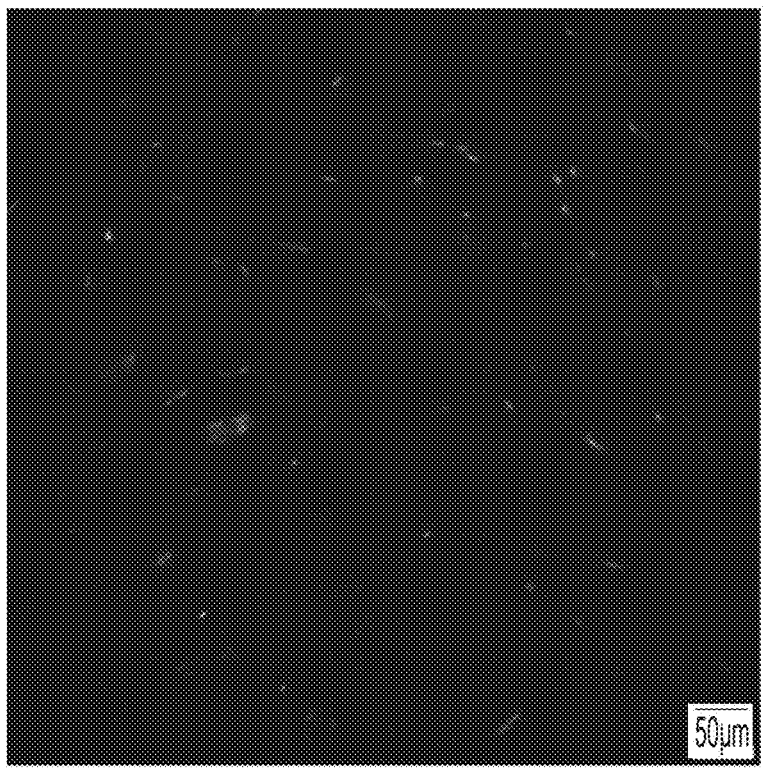
FIGS. 12A and 12B are images depicting immunofluorescent staining of HLA class I antigens, according to an illustrative embodiment.
Figure 12B:
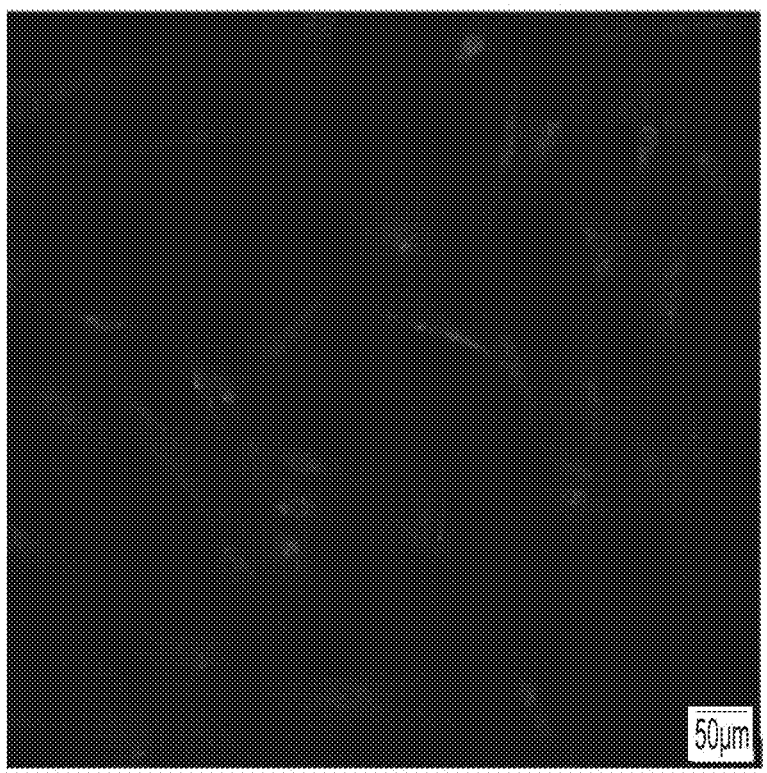

Green fluorescence is found on the cell surface of human fibroblasts. The distribution of green fluorescence is uneven (FIG. 12A). The finding suggests HLA class I antigens mainly express on cell surface of human fibroblasts. Red fluorescence of mitochondria labeled by MitoTracker Red is mainly seen in cytoplasm (FIG. 12B). These findings show that mitochondria have no or very low expression of HLA class I antigens. In addition, the same immunofluorescent technique was used to examine HLA class I antigens of the isolated mitochondria of fibroblasts. There was no positive green fluorescence in the mitochondria. These results suggest that mitochondria of human fibroblasts do not express HLA antigens and could be used for allogeneic MOT with no need of HLA antigen match.

Human leukocyte antigen (HLA) is associated with rejection or acceptance of organ or cell transplantation. Mismatch of HLA between donor and recipient often results in rejection of cells and organs after stem cell therapy and organ transplantation. In the experiments described herein, it was found there is no expression of HLA in mitochondria. Thus, it is possible to transplant mitochondria from any healthy donor to recipients without HLA match. There is no problem of donor sources. This is a significant advantage over stem cell therapy and organ transplantation which require HLA matching of donor and recipient.

Human Fibroblast Mitochondria Enter into the Mitochondrial DNA-Defective NSC-34 Easier than Healthy NSC-34

Figure 13A:
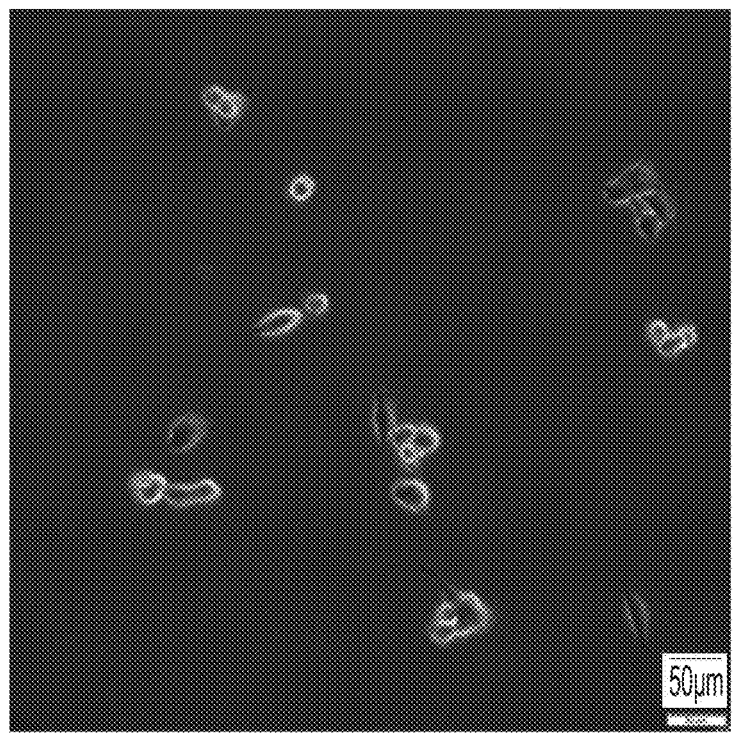
FIGS. 13A, 13B, 13C, and 13D are images showing the isolated mitochondria from human fibroblasts labeled by MitoTracker Red are transferred into mouse motor neural NSC-34 cells after 12 hours of co-culture, according to an illustrative embodiment.
Figure 13B:
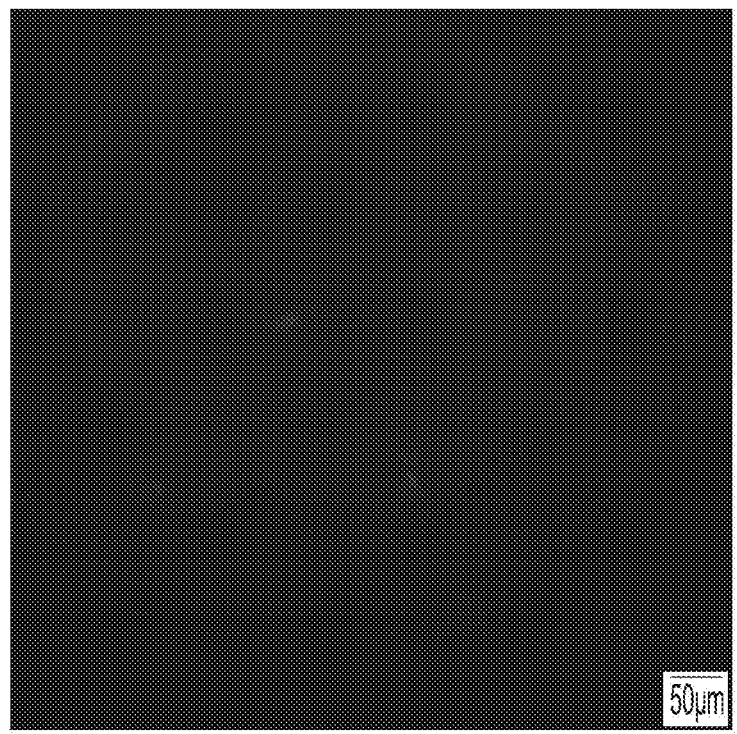
Figure 13C:
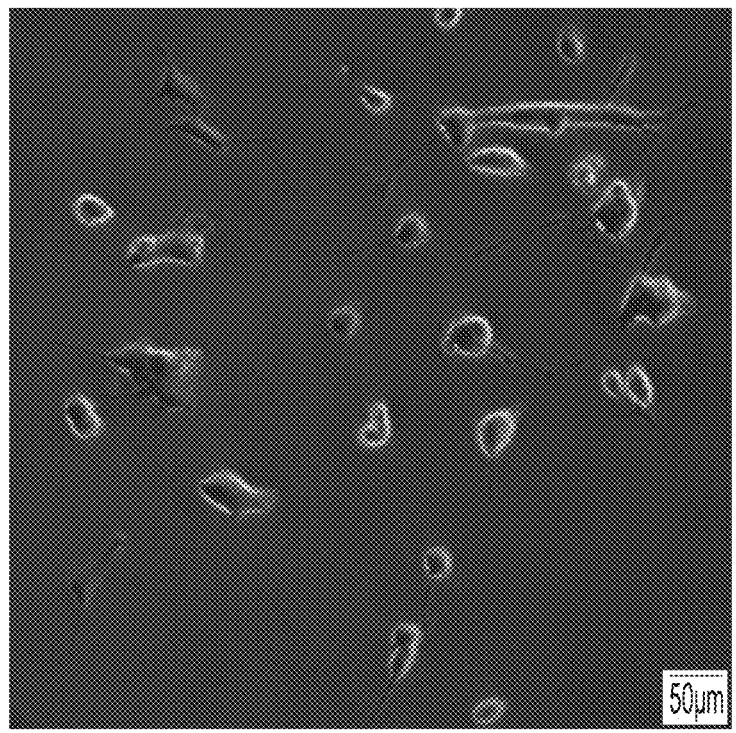
Figure 13D:
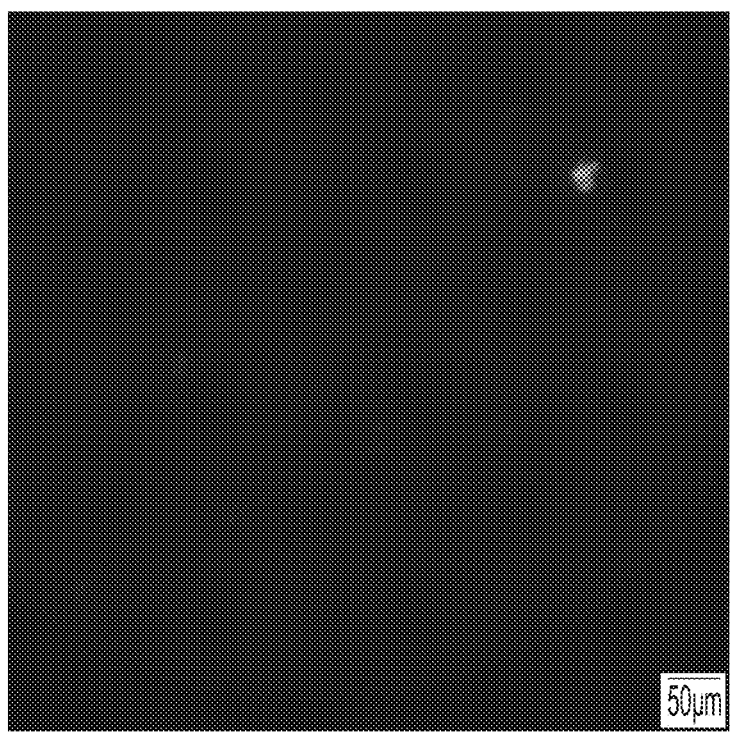

NSC-34 cell line provides a motor neural model for in vitro study. After 12 hours of co-culture of NSC-34 cells with the isolated mitochondria labeled by MitoTracker Red, red fluorescence is found in the NSC-34 cells (FIG. 13A, 13B). This suggests that human fibroblast mitochondria enter into mouse motor neural NSC-34. Moreover, higher intensity fluorescence was found in the EtBr-treated NSC-34 cells (FIGS. 13C, 13D). This shows fibroblast mitochondria more easily transfer into the mitochondrial DNA-defective NSC-34 cells. These results reveal sick tissues and organs uptake more fibroblast mitochondria than healthy tissues.

It is possible to quantify the preferential update of mitochondria by defective cells vs. healthy cells as follows. The fluorescent intensity of the pre-labeled mitochondria can be measured in defective cells and healthy cells after co-culture of the cells and the pre-labeled isolated mitochondria by florescent microscopy. The intensity can then be compared between defective cells vs. healthy cells.

Clinical Study I

Initial Clinical Results of Mitochondrial Organelle Transplantation (MOT) in Two Human Patients with Amyotrophic Lateral Sclerosis (ALS)

Mitochondrial organelle transplantation (MOT) was initially performed in two ALS patients, one female and one male. The female patient is a 58 year old white female who has had progressive ALS for over 3 years (at start of treatment). She had failed all previous treatments. She signed an informed consent for this experimental therapy after several long consultations about the procedure and research evidence of proof of principle for possible efficacy. The male is a 48 year old white man with progressive ALS for 3 years (at start of treatment). He was informed, wanted to try MOT and signed the detailed consent.

Described in this set of initial clinical results (Clinical Treatment A) for the female patient are 6 MOT procedures that began in June 2019. The procedures were performed at about 5-6-week intervals. Prior to treatment, she had muscle strength testing of her leg muscles, quadriceps and hamstrings. The first 4 transplants were only done in leg and upper arm muscles. Multiple injections of viable isolated allogeneic fibroblast mitochondria in our buffered storing solution were given in the muscles in multiple areas. With the 5$^{th}$ and 6$^{th}$ procedures, she had the muscle injections and also received 5 ml of isolated mitochondria in the storing solution intravenously.

Figure 14:
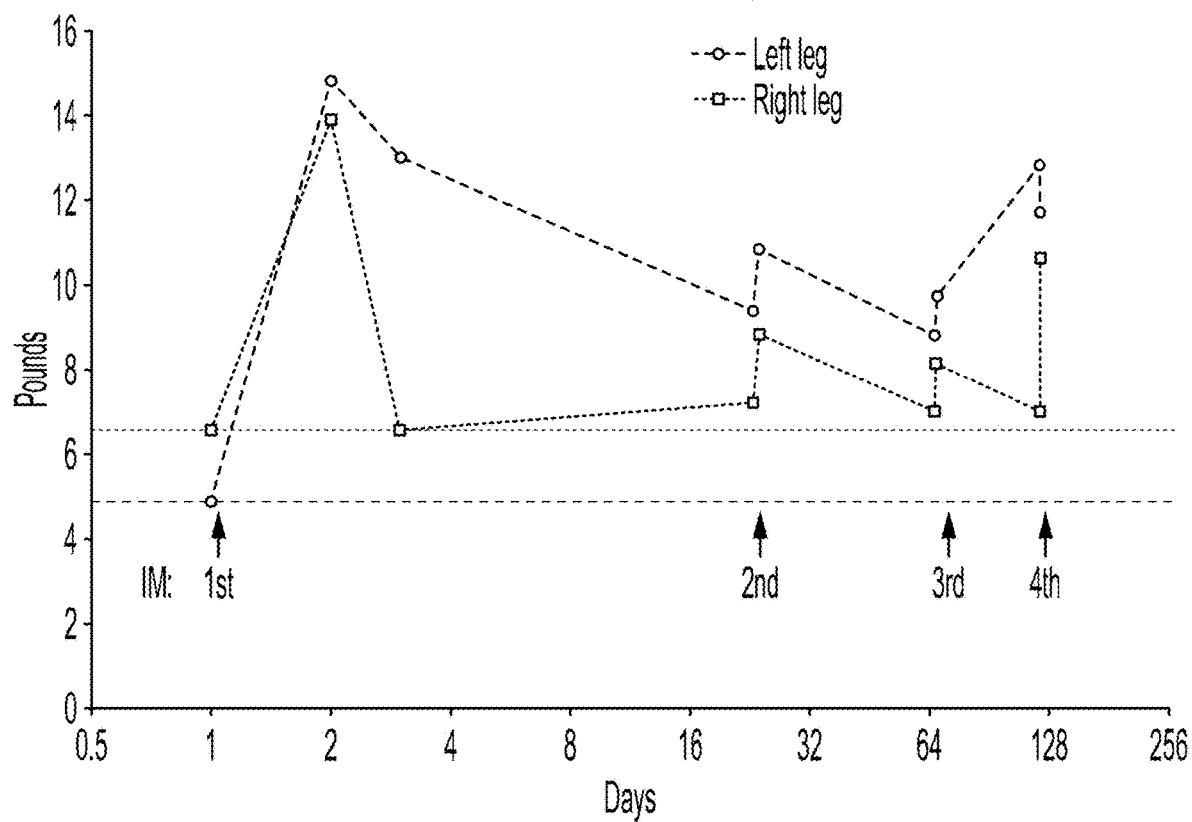
FIG. 14 is a graph showing that injection of human fibroblast mitochondria improves muscular strength of leg quadriceps in ALS patients, according to an illustrative embodiment.

The patient had no adverse events, and there have been no signs of rejection, autoimmunity or infection. There has been improvement in muscle strength (FIG. 14) and her mobility with tremendous improvement in her hope and mood. The biggest improvement has been in her sensory sensation. At presentation she had hardly any feeling in her arms and legs and needed no local anesthesia for muscle injections. After the 3$^{rd}$ transplantation sensation and sensory stimulation had returned and has remained normal. It is believed the sensory return has helped motor neuron function. A great result of the MOT is that the progression of disease stopped and her sensation, strength and mobility have improved. Her treatment is a work in progress and the MOT is complemented by sensory stimulation and supplements for mitochondrial health. She is receiving an iron chelator weekly because of high serum ferritin, an indication of motor neuronal iron overload. Her next MOT is planned for mid-March 2020 after a 3-month interval from the last MOT. Her results reveal MOT can palliate, stabilize, and possibly reverse motor neuron degeneration in ALS. The lady is to the best of our knowledge the first human to receive a MOT of allogeneic fibroblast mitochondria for ALS.

The male patient is a 48-year-old white male with progressive ALS for over 3 years (at start of treatment). He has severe generalized muscle weakness with the bulbar ALS variant. He talks very slowly and it is very difficult to understand him when he speaks. He received his first MOT treatment on Dec. 11, 2019. He had multiple injections of isolated fibroblast mitochondria in legs, upper arms and posterior neck muscles. He also received 2 ml of the isolated mitochondria in the storing solution intravenously. He has had no adverse events and within 2 hours of the treatment he was talking faster, stronger and could be understood. Five days later he could get out of bed without assistance and could walk without help to the bathroom. He went deer hunting with his sons, but did use his special chair. His mood, spirits and attitude has improved and he is more positive and very anxious to continue MOT. He states that he has had a tremendous burst of energy. He could not hold up his head and drooped all the time, but now his head does not droop.

In the seven procedures of mitochondrial transplantation in the two patients discussed above (Clinical Treatment A), the first 4 injections were intramuscular. The last 3 injections were combinational intramuscular (⅔ mitochondria from approximately 100 million fibroblasts) and intravenous (⅓ mitochondria from approximately 100 million fibroblasts). The last 3 injections show better response (muscular strength, sensation, energy).

In summary, the experience with MOT in these two ALS patients in Clinical Treatment A has been positive for treatment of and/or arresting progression of their disease. Some of the important findings are: (1) Allogeneic mitochondria can be safely transplanted to humans without HLA antigen match. (2) They cause no autoimmunity. (3) ALS symptoms are improved. (4) MOT may extend longevity or palliation to possibly cure ALS. And (5) MOT may be performed for treatment of other neurodegenerative diseases, such as, Parkinson's disease, Alzheimer's, muscular dystrophy, and other mitochondrial disorders.

Clinical Study II
Longer Term Clinical Results of MOT in Five Human Patients with ALS A total of five patients received the mitochondrial organelle transplantation (MOT) treatment with a total of 21 treatments to date (Clinical Study II described here is inclusive of Clinical Study I, an initial study involving two of the five patients, described above). Patient Code No. A5 received treatments dating back approximately 1 year with no adverse effects to date. All patients have reported no adverse effects with some reports of pain during the injection procedures.

In all cases, patients have reported increased ability to perform numerous tasks through improved muscle strength, control, and movement. Additionally, they all report higher energy levels and improved mood after the MOT treatment. These reports have been verified through videos, tests, consultations during clinical visits, and further supported by the clinical notes of the clinician.

In several cases, the patients have reported that overall disease progression has been arrested, and this has been observed and documented in observations from the clinical team. In three of the five patients, videotaped sessions conducted with the clinical team on various measures of improved health and functionality, indicate disease progression has been arrested.

Patient Code No. A5

A 58-year-old female from the south, previously in good health, with no known pre-existing conditions, presented with confirmed diagnosis of ALS in June 2019. She was diagnosed in 2016, 3 years before beginning treatment with mitochondrial organelle transplantation (MOT). Upon a routine physical examination there were no remarkable indications. She presented with primary symptoms in her lower body and to a lesser degree her right arm and lesser still the left arm. She had little to no sensation or motor control from the waist down, but had fair use of arms and hands, and her voice was good.

Jun. 3, 2019—Patient Intake Exam

Intake exam completed physical exam and she appeared in good condition except for the ALS. Muscle strength tests were completed as a baseline.

Jun. 4, 2019—$1^{st}$ Treatment

The first patient ever that we are aware of to receive isolated allergenic mitochondrial from fibroblast.

Prior to the treatment, we took videos with her permission, completed muscle strength testing, and identified 18 areas for injection. Each location was marked and prepped, and 1% Xylocaine was used to provide numbing at the injection sites. Each of the 18 sites were administered 3/10 cc of the mitochondria solution. There was minimal bleeding from puncture wounds, and they were cleaned with Betadine and wrapped with sterile dressing. The patient was observed for over 3 hours with no adverse events. No sign of any allergy and these mitochondria were allogeneic from fibroblast human cell line.

During observation, she started noticing warmth and heat in her legs and on the right lower leg where she had no feeling before. She began to have some feeling before leaving the office and on the left leg she said it felt stronger and she was able to raise it up and flex it and extend it without difficulty. No toxicology or adverse events were observed. This patient scheduled a follow-up each of the next two days.

Jun. 5, 2019—Day One after Treatment Follow-Up

The patient arrived in the morning for follow-up. Initial indications were positive, and she reported that she felt better. The patient reported tingling and warm sensations in both legs. She was able to get out of the bed by herself in the morning, which is more than she was able to do previously, and she was standing. Muscle strength was tested with improvements as shown in Table 3a—Treatment 1. She indicated no adverse effects, no toxicity, and no fever. We have achieved an objective proof that MOT injected into the quadricep muscle has improved that muscle strength in an ALS patient.

Jun. 6, 2019—Day Two after Treatment Follow-Up

The patient arrived reporting no adverse effects, no toxicity, and no fever. We tested and recorded muscle strength, discussed self-monitoring guidance upon her return home, and scheduled her next treatment for June $27^{th}$. After release, the patient was called several times before returning for treatment, with no adverse effects reported.

Jun. 27, 2019—$2^{nd}$ Treatment

The serum ferritin level was recorded before treatment as 228 ng/mL, and transferrin was 293 mg/dL (ref range 200-360). Upon arrival we evaluated her physical condition and performed muscle strength testing again. The results indicated a slightly better pre-treatment baseline than her first baseline on June 4.

When tested during follow-up on June 28, the numbers were overall slightly better than before treatment on June 27. The areas of improvement were not as dramatic as the day after the 1st treatment but were improved overall as shown in Table 3a—Treatment 2.

There were no adverse effects, no toxicity, and no fever experienced, and the night of this treatment, the patient sent a text message indicating she was able to get out of the bed and walk with greater ease.

She did experience some tingling and warmth in her legs as previously observed, but not as dramatically.

We received her CBC and iron work-up. The CBC was fine. Interestingly in the iron work-up, the iron binding capacity, saturation serum, and unsaturated IBC and total IBC in the calculated iron saturation were all within normal levels (WNL). However, her serum ferritin was high.

For subsequent treatments and patients iron metabolism are being observed. Chelation therapy using deferoxamine or similar will be considered. The patient was notified of all the test results and scheduled a next therapy treatment the first week of August.

Regular follow-ups were conducted with the patient to track her progress and her symptoms. A call on June 30 indicated that she and her family noticed improvements since the 2nd treatment.

Jul. 7, 2019—Special Note in File

A detailed review of the muscle strength tests was completed by the team, and we have added these charts to her file. The positive news is even though there is some variation at certain times, the overall trend is increased muscle strength in all areas that were injected during treatment.

Aug. 8, 2019—3rd Treatment

Prior to treatment, muscle strength was tested as shown in Table 3a—Treatment 3. The patient and her family indicated that she was definitely better than before treatments were started in early June. The patient observed that she was able to get up out of bed easier now and turn over in bed without help.

For this transplant, there were several areas in the quadriceps of both legs, some ham strings and buttocks as well as both arms and forearms that were selected. Following the treatment, there were no adverse events or toxicity experienced. During the evening after the treatment when checked on she was doing great. She was able to grasp her bottle with her left hand which was an additional improvement. There were no calls or issues during the night.

During her follow-up the day after treatment, muscle strength was tested which indicates a slight drop off, but still higher than her original baseline.

Between treatment consultations no adverse effects or issues were reported, yet with some continued improvements in her daily abilities.

Oct. 2, 2019—4th Treatment

Her latest lab work CBC showed there is eosinophils WNL. For this treatment she was given 30 injections in quadriceps, hamstrings, buttocks and in the forearms and one area in the right bicep area. For the first time, we utilized the hep-lock placed in preparation for any adverse event to administer 5 cc slowly through the IV port. No adverse effects were reported, and she returned for follow-up enthusiastic about her overall progress with the treatment and her improvements. Muscle strength was tested before treatment and the next day in a follow-up with an overall slight improvement as shown in Table 3a—Treatment 4.

During checks between treatments, she reported no adverse events or issues. By early November, she still reported good sensation in both legs but not in her hands and arms. She retained her muscle strength in her legs. There were some percentage of elevated eosinophils but when the absolute count is done it was normal. She planned to return on the 6th for her next treatment.

Nov. 6, 2019—5th Treatment

Oct. 30, 2019 The serum ferritin level was recorded before treatment as 362 ng/mL.

She presented for her 5th MOT today. She is doing well. The disease has pretty much stabilized and in some areas markedly improved, especially with her sensory and sensation. During her first MOT treatment she did not have enough sensation to feel the intramuscular injections, but as treatments continued, she has confirmed feeling the injections at increasing levels. Prior to treatment, muscle strength tests were completed. For this treatment, we began by slowing administering 5 cc of cold mitochondrial in the isolation media over 6 minutes. It was very cold, and she developed an immediate headache and felt a little funny but no serious adverse reaction. We laid her down, vital signs were good. We elevated her legs and over approximately 30 minutes her symptoms subsided. For intramuscular injections, the quadriceps were injected but not as much as last time on both legs we injected the hamstrings on both legs and this time we injected down toward the tibialis muscle on both legs. We also injected the biceps. She did well and was observed for over 3.5 hours before being released, with no adverse events or issues. During follow-up on November 7, we completed muscle strength tests for comparison as shown in Table 3a—Treatment 5. Some places were improved, some were stable, and some were slightly worse. We have scheduled the next treatment for December 11, after which there will be a 3-4-month break from treatments while condition and symptoms are monitored. It appears now is the time to add another patient to our protocol.

During the three days November 8-10, we spoke several times and she reported doing extremely well but had lightheaded and dizzy on several occasion. She reported that she had more strength in her legs than ever. As of November 11 she reported feeling fine with no dizziness. Additional calls prior to the 6th treatment she reported no side effects or adverse events but continued strength especially in her legs and arms.

Dec. 11, 2019—6th Treatment

Dec. 4, 2019 The serum ferritin level was recorded before treatment as 290 ng/mL, and the transferrin was 271 mg/dL She presented today for her 6th transplant and biotherapy. She reported that she was doing much better and has a lot of sensation back, more than she had even in the previous month, especially in her feet. She reported increases in muscular strength and her stamina seemed better too. We injected her quadriceps, hamstrings and her upper arms, and gave 5 cc slowly through IV. The patient experienced another episode of headache and dizziness, but it passed as it did in November. There were no adverse effects noted during post-treatment observation and she was released for the night. During our evening call she indicated she was feeling much better and had taken a nap.

When she arrived on December 12 for her follow-up the day after treatment, the patient reported that she was feeling great, energetic and better than the past several weeks. We also discussed her taking an iron chelator. We are exploring the role of iron metabolism in these neurons which may contribute to Mitochondrial dysfunction. We proposed giving her 500 mg of Deferoxamine one a week for 4-6 weeks to be administered by injection from her local practitioner, which was completed.

Between Treatment Patient Interactions

We spoke with this patient and on occasions with members of her family about her condition and her progress. There have been no adverse events and no reported episodes of severe dizziness or headaches. She was originally scheduled to return on Mar. 11, 2020, but because of the COVID-19 pandemic that was postponed until mid-April.

On March $3^{rd}$ a long telephone consultation was conducted. She reported that she has stabilized her disease progression and was pleased with the progress she had made since June of last year, but she still has periods of time when she is not as active. She reported she is still doing Physical Therapy and getting muscle stimulation.

On April $10^{th}$ serum ferritin test was received and had dropped back to normal range. We called the patient to let her know the good news.

We requested a repeat to the bloodwork and at the end of the week we received them; her serum ferritin is down to 181.8 in the normal range. She reported a little slowing of improvement but overall, she was doing well.

Apr. 15, 2020—$7^{th}$ Treatment

She presented on April 15 for her seventh transplant, four months since her last procedure. She reported a little more fatigue recently. We think we have stopped her rapid progression, but she was feeling some more weakness, she thought she may be regressing somewhat. She was very anxious to get the transplant. We started the IV and we marked all of the areas selected for injection in the muscles, and we had almost 8 cc of mitochondrial isolation fluid in syringe that we gave slowly through IV over a period of time. We injected 3⁴⁄₁₀ cc of mitochondrial isolation fluid in each injection sites and two on each side posterior to the area right and left. We administered three injections down the forearms on both sides and five injections in the quadriceps both sides one centrally and one anteriorly two laterally and two mediately on both sides. The treatment was tolerated.

In follow-up the next morning, she reported feeling more energetic and said that her left side felt much better and stronger. Things are moving in the right direction for her and we believe this therapy has stopped the rapid progression of ALS in this patient.

She texted that after arriving home she felt great and she feels like the last transplant on April 15 was one of the better ones. She reported that everything is working better for her she has more energy. We observed marked improvement and believe progression of her disease has stopped. She reported her desire to continue on this protocol, and we proposed at least two more treatments at six-week intervals followed by another 3 to 4-month break may be a good protocol for this patient.

Jun. 17, 2020—$8^{th}$ Treatment

Jun. 17, 2020 the patient arrived for her eighth transplant procedure which marks one-year since her first treatment which was on Jun. 4, 2019. During this year we have accomplished a lot to help this patient, including stopping progression. For this treatment we started an IV, planned the areas that we were going to inject and created a diagram in her chart showing the areas of injection. We injected two in the upper neck on both sides somewhat posteriorly. Several additional injections were performed in the upper arms, lower arms and hands and thumb areas as well as in the quadriceps and hamstring areas and in the calves. She tolerated the treatment well when we gave the IV infusion even though it was cold. We gave it very slowly and she did not have any of the headache and dizziness as before. This was the first IV given that she did not have headache and dizziness. During post-treatment observation, she started noticing warmth and tingling (humming feeling as she calls it) in her legs. This observation was considered a good sign with this patient.

We drew blood for a new ferritin reading before disconnecting the IV. There were no reported adverse effects or events. During the follow-up the next day, she reported feeling stronger and looked well. We had a long discussion with her and her husband about her progress over this past year. They agreed to allow video documentation of our discussions to use in conjunction with her research results.

The patient's progress will be monitored via phone until she returns in approximately 6 weeks for her next treatment.

Muscle strength tests were conducted before and after injections for the first five treatments using the ActivForce Digital Dynamometer System as recorded in Table 3a below:

TABLE 3a

Muscle Strength Test-Patient Code A5

| Treatment 1 | Left Leg | | | Right Leg | | |
|---|---|---|---|---|---|---|
| Jun. 4, 2019- Jun. 5, 2019- Jun. 6, 2019 | Before Treatment Baseline | Day After Treatment | 2nd Day After Treatment | Before Treatment Baseline | Day After Treatment | 2nd Day After Treatment |
| Knee Lift | 7.0 lbs. | 11.9 lbs. | 5.6 lbs. | 7.4 lbs. | 9.91 lbs. | 6.7 lbs. |
| Lower Leg Lift | 4.9 lbs. | 14.8 lbs. | 13.0 lbs. | 6.5 lbs. | 13.9 lbs. | 5.6 lbs. |
| Hamstring | 8.5 lbs. | 6.5 lbs. | 4.0 lbs. | 9.7 lbs. | 8.5 lbs. | 7.0 lbs. |
| Heel Press | lbs. | 18.0 lbs. | 20.2 lbs. | lbs. | 23.2 lbs. | 18.4 lbs. |

No Heel Press on 6/4

Table 3b shows Complete Blood Count (CBC) with Differential (complete blood panel) also run at or near same date as ferrin from June 2019—April 2020, for Patient A5.

TABLE 3b

Patient Code A5 - Serum Ferritin level as recorded before treatments

| Jun. 27, 2019 | Oct. 30, 2019 | Dec. 4, 2019 | Jan. 16, 2020 | Apr. 8, 2020 | Jun. 17, 2020 |
|---|---|---|---|---|---|
| 228 ng/ml | 362 ng/ml | 290 ng/ml | 205 ng/ml | 188.8 ng/ml | 362 ng/ml |

Patient Code No. A4

A 48-year-old male from the southeast, previously in excellent health, served honorably in the U.S. Armed Forces, worked for a major transportation delivery company, and coached recreational league ball in his hometown. He presented with a confirmed diagnosis of ALS in mid-December 2019 for treatment. He experienced symptoms beginning in 2016 and was diagnosed in 2018. He has been prescribed Riluzole and Edaravone for ALS but has not noticed significant benefits. He is also taking Alprazolam, Naproxen, fluoxetine HCL, Tylenol, and Melatonin. Testing on December 9 indicated his serum ferritin level was 319 ng/mL, and the transferrin was 264 mg/dL.

A complete evaluation was conducted on Dec. 17, 2019. He had significant deficits, a very difficult time talking, virtually no use of either of his arms and hands, could not hold his head up and has significant weakness in his legs and lower body.

For the treatment the patient was started on an IV in the left hand. Finding an appropriate vein was difficult but we managed to get one on the left side and suggested that he explore getting a Med port installed for his safety ongoing in case of an emergency and to make treatments easier. We gave him injections in the arms on both sides in the deltoid and triceps areas, forearms, the posterior neck area on both sides, as well as quadriceps and calves. He had approximately 30 total intramuscular injections and 2 cc of the MOT via the hep-lock IV. The patient had no adverse events or effects. He reported in the follow-up feeling much better and he believed he was stronger. Post treatment follow-ups by phone mostly with the caregiver indicated that this patient was doing better. He had a lot more energy, could walk better, move his arms better, and turn on the shower knobs. His Med port was installed on January 10. A follow-up call Indicated he was doing well. Five weeks after the first MOT treatment, the patient arrived for the 2nd treatment. Upon observation of the patient, we noted how much better he appears and that his first treatment has lasted.

The patient was more mobile, able to get out of bed by himself, goes to the bathroom by himself, and has more energy, and his head and neck does not lean forward anymore as it did prior to the first treatment. He still had significant issues with speech, but his speech was better, still very slow and slurred but you can understand him better and it is a little more forcible. For this treatment, injections were performed in the quadricep muscles both sides, the calves mediately on both sides, biceps in his forearms on both sides, and posterior neck muscles on both sides. He had the Med port, which made it easy to access, and he received a slow IV push for 5 to 6 minutes of 2 cc MOT. He tolerated the treatment well and observation indicated no adverse events or side effects. He reported the following morning for follow-up, and he was not feeling well. Upon examination we determined he ate two large meals with lots of carbs and he drank a good bit of beer. He hydrated with Gatorade and we instructed him to rest, not eat as much and to return tomorrow. He reported in the morning on the 2nd day after MOT feeling much better than the previous day. He reported feeling very positive about his improvements. In fact, last night he felt so good that the patient made a short video of himself dancing, which he had not done in a long time. The patient was asked to stay hydrated.

Between treatment telephone conferences the patient reported no adverse events no side effects but continued improvement on various levels in his condition. He reported attending a rally in his hometown last weekend and has been able to do more than he had been doing previously. He reported being excited about his next transplant and lithium orotate was added to his protocol.

On March 18 the patient is back for his 4th MOT transplant we accessed his med port with some difficulty. We managed to get a good return and stabilized it. We gave him almost 5 cc of isolation fluid MOT through the IV port. For intramuscular injections, the right and left sides of his neck, both deltoid and triceps regions and muscles, bicep muscles and forearm muscles, we injected several areas of quadriceps bilaterally, more on the left, which is his weakest area and both calves. He tolerated the treatment well. Follow-up resulted in no adverse events as did between treatment telephone consultations.

April 22nd the patient reported for the 5th MOT transplant. They had extreme difficulties in travel because of the COVID-19 pandemic. The patient stayed at the airport the night before treatments and was fatigued the day of treatment but in good spirits. All normal treatment preparations were performed. As part of the procedure a diagram is included in the chart to indicate injection sites for this treatment, including the neck, upper arms, forearms, calves and thighs were the predominant locations of injection. We administered approximately 8 cc of MOT over an 8-10-minute period through the IV Med port. No adverse impacts were evident in any of the predetermined locations. The patient received intramuscular injections then was observed for approximately 1.5 hours while receiving IV fluids and water for hydration. We released him without incident; no adverse events or effects were observed. As with previous treatments however during the IV delivery of the treatment, this patient has had pain to appear in his lower back about halfway through the IV treatment delivery. There is no specific explanation for this pain in this area at the same time during each treatment. One possible explanation being the Mitochondria are going right away to this area of his body because of the problems he has in his spine. We checked on him during the evening and he was doing well. He did not come to the office for his normal day-after follow-up in order to depart on a 6 a.m. flight. We indicated they should call with any issues.

During multiple telephone consultations between treatments, the patient reported no adverse events, no side effects, and no fever, but continues to experience improvements.

He reported on May 27th for his 6th MOT treatment. Since he began treatments in mid-December, he has made a lot of progress and is doing better in many ways. He still has a difficult time with speech, and it is hard to understand him consistently, but his speech is much better than it was six months ago. The patient reported VA physical therapy testing done at his home prior to any MOT treatments yielded a score of 12. He was retested approximately two weeks ago with a score of 28. This is a significant improvement in approximately 6 months.

For this treatment, he received 34 intramuscular injections of MOT 3$^{4}$/10 cc each and 8 cc through slow IV push over approximately 10 minutes. As with previous treatments through IV, about 4 cc into it, he again experienced severe pain in his lower back spine area but this one seemed more intense. We stopped the injection for a while and moved onto the intramuscular and then finished the IV administration at the end of treatment. No adverse events were experienced or reported during observation. When checked on during the late afternoon and in the evening, he was doing well. He reported the next morning that there were no adverse reactions. He was feeling well, strong, and he now holds his head up without difficulty. He was instructed to stay hydrated and report any issues immediately. Telephone consultations with this patient continue to be positive. He is maintaining his energy and his mobility functions gained through MOT. While he still has significant issues, his overall quality of life and control over his daily activities has shifted dramatically in his favor from when he first reported to us in December of last year. We will maintain follow-up via phone and will consult soon regarding when we believe he should be scheduled for his next MOT.

Patient Code No. A3

A 68-year-old male from the south, previously in reasonably good health, presented with a confirmed diagnosis of ALS issued in December of 2019. Prior to retirement he was a law enforcement officer for more than two decades. He has Type 2 Diabetes but not uncontrolled, and is treated for high blood pressure, also not uncontrolled. He experienced symptoms for two years prior to diagnosis; primarily in the left arm and hand. He dismissed the onset of symptoms as the probable development of arthritis. As the pre-diagnosis period moved well into the second year, he began having other symptoms, primarily muscle twitches or fasciculations. He was tested and seen by several doctors in Huntsville, Ala. and in Atlanta, Ga., who confirmed diagnosis and lack of meaningful treatment to improve his condition. He has been prescribed Riluzole, but as with our other patients, has seen little to no real benefit. He is also taking Amlodipine, Alprazolam, Hydrochlorothiazide, Metformin, and Toprol XL for his other pre-existing conditions. His transferrin was recorded as 241 ng/mL.

Because his greatest difficulty is with usage of his left arm and hand, and to a lesser degree the right arm and legs, we identified injection sites to address his current symptoms and all were prepped. He was given 2.5 cc through slow IV push, and 3/10 cc intramuscular injections in his shoulders, arms, hands, and legs. Sites focused on the left arm and hand with more injections than the right arm which were focused on triceps and biceps. We mirrored injections in both legs at the quadriceps and calves. He was monitored and hydrated for more than two hours after treatment, and there were no adverse events or reactions.

His day-after follow-up appointment did not reveal any side effects or adverse events. In telephone consultation the following week, he indicated he was still feeling great and had much more grasping capability in his left hand. Later follow-up calls indicated slow and continued improvement.

He was scheduled for his 2nd MOT on April 1, but the current COVID-19 pandemic forced a delay. He did return on May 20, more than 3½ months after his first MOT. While he did lose some of the initial improvements, he was still better than before the first treatment. We completed standard prep and started the hep-lock IV in preparation for the treatment. All of the areas treated previously were used and additional locations in the legs, arms, and in his left hand including between the thumb and index finger. A total of 30 injections were given and 8 cc through IV over 9 minutes. The treatment was tolerated well, with no adverse events or side effects. When he returned the following day, he was much improved and pleased to report that after treatment yesterday and this morning, he was able to open the car door with his left hand, which he had been unable to do for over a year.

His 3rd MOT treatment was June 24. The patient reported that he feels he has retained benefits from the last MOT feeling stronger, with the fasciculations occurring only on rare occasions. He reported excellent use of his left arm and hand. Observation of the patient indicated that his breathing is good, his walking is good, and he was getting better sleep than previously reported. The injections and IV slow push of his second treatment were repeated which was tolerated without any adverse events or reactions. His follow-up appointment confirmed feeling better overall with continuing improved strength in his arms, hands, and legs. He reported feeling pleased with the progress and wishes to continue this treatment protocol. He will return in 4 to 6 weeks.

Patient Code No. A2

A 73-year-old male from the south, previously in good health, presented on Apr. 8, 2020, with confirmed diagnosis of ALS. He has been prescribed Riluzole, a currently available medication for the possible slowing of symptom progression in ALS patients. He has not experienced any significant slowing in the progression of his symptoms through use of this medication. Prior to treatment, his symptoms were reviewed, and an ALS Functional Rating Scale was completed. He scored 37 on the scale, with 6 of 12 criteria impacted. His greatest deficits are his right arm and hand, which have the greatest degree of weakness and loss of use. He does have issues with his other limbs, but to a lesser degree. The first treatment focused on the right arm and hand as well as quadriceps and thighs of both legs. Standard site prep and identification were completed, and the hep lock IV was started. Approximately 20 intramuscular injections of 3/10 cc and 5 cc slow push delivery at the IV were administered. The treatment was well tolerated, and no adverse effects were experienced during the observation period in the office, or after release. Upon leaving the office after the first treatment approximately two hours after we started, his wife observed he was walking with greater ease and stability. The day-after follow-up and between treatment consults with this patient yielded positive results with some improvements noted in both strength and functionality of the legs and the right arm and hand. The serum ferritin was reported as 190 ng/mL, and the transferrin was 259 mg/dL.

This patient received additional treatment on May 6 and June 10 with both treatments consisting of 8 cc slow push IV and 30 intramuscular injections. Areas of injection included each side of the posterior neck, upper arm, hand, and thumb on both sides, both legs in the thigh area, quadriceps, hamstrings and calves. There were no adverse events or side effects. Treatments were well tolerated and continued incremental improvements in strength and functionality have been realized by this patient. The patient expressed his desire continue the treatment protocol and we will work to schedule him every 4-6 weeks.

Patient Code No. A1

A 30-year-old male from the west coast presented for treatment in May 2020 with a diagnosis of ALS. He experienced symptoms in March 2019 and was diagnosed in August 2019 after testing, including MRI, blood tests, and Electromyography (EMG). He had been prescribed Riluzole but did not experience reduction in progression of his symptoms. He had also been given a stem cell treatment with little to no positive results. His serum ferritin level was recorded before treatment as 381 ng/mL, and the transferrin as 239 mg/dL Upon a routine physical examination there were no remarkable indications. He scored 44 on the ALS Functional Rating Scale, with primary symptoms in the left hand and arm, to a lesser degree in the right hand and arm, and lesser yet in both legs. He was able to walk well. Muscle strength tests were conducted using an ActivForce Digital Dynamometer System before and after treatment with mitochondrial organelle transplantation (MOT) as recorded in Table 4 below:

TABLE 4

Patient Code A1
Muscle Strength Test

| Treatment 1 | Left Leg | | Right Leg | |
|---|---|---|---|---|
| | Before Treatment Baseline | Day After Treatment | Before Treatment Baseline | Day After Treatment |
| Knee Lift | 20 lbs. | 21.1 lbs. | 18.9 lbs. | 16.2 lbs. |
| Lower Leg Lift | 17.1 lbs. | 15.5 lbs. | 13.5 lbs. | 18.2 lbs. |
| Hamstring | 26.1 lbs. | 28.4 lbs. | 26.8 lbs. | 28.3 lbs. |
| Heel Press | 77.6 lbs. | 91.9 lbs. | 90.1 lbs. | 96.4 lbs. |

At the first treatment of this patient, an IV was started and 8 cc of the mitochondrial organelle transplantation (MOT) was administered through the IV over a 9-minute period. Areas identified for intramuscular injection of MT were marked and prepped (including administration of Xylocaine to deaden the injection sites). For this patient, injection sites included posterior neck, shoulders, upper arms around wrist, hands and forearms, thighs and calves. About 29 injections of 3/10 cc were administered to those muscular areas. No problems were observed. He was given an additional 250 cc of push IV of fluids. The hep-lock intravenous (IV) catheter was left in place during post treatment observation for approximately 1.5 hr. During observation he was encouraged to drink water, no adverse events were observed and the hep-lock was removed and dressed in a pressure wrapping to be removed later that evening. At his scheduled 24-hour follow-up exam, muscle strength was re-tested with overall signs of improvement. His walking was better, and he reported regaining the ability to deliver a 'thumbs up' with the left thumb which he was unable to extend the thumb or give a 'thumbs up' the two previous days but could during this day after follow-up. His grip in the left hand was also much improved from the two previous days.

Post-treatment telephone follow-ups with this patient were positive with continued stability in the improvements from the first treatment. His second MOT will be late July.

SEQUENCES (nucleotide sequences)

```
> CTAGCCGCAGGCATTACTATAC                                    SEQ ID NO: 1

> TGTCAAGGGATGAGTTGGATAAA                                   SEQ ID NO: 2

> GCCGTAGCCCAAACAATTTC                                      SEQ ID NO: 3

> CGTAACGGAAGCGTGGATAA                                      SEQ ID NO: 4

> CTGAGTCTCCCTTGGATCTTTG                                    SEQ ID NO: 5

> AGGGCAGGTGAAACTGTATG                                      SEQ ID NO: 6

SEQ ID NO: 7 (see Table 1)
> ACTB, FWD primer, GAGGTATCCTGACCCTGAAGTA

SEQ ID NO: 8 (see Table 1)
> ACTB, REV primer, CACACGCAGCTCATTGTAGA

SEQ ID NO: 9 (see Table 1)
> ACTB, Probe, TGGCATTGTTACCAACTGGGACGA

SEQ ID NO: 10 (see Table 1)
> MT-CO1, FWD primer, ACCACCATCATTTCTCCTTCTC

SEQ ID NO: 11 (see Table 1)
> MT-CO1, REV primer, CTCCTGCATGGGCTAGATTT

SEQ ID NO: 12 (see Table 1)
> MT-CO1, Probe, AAGCAGGAGCAGGAACAGGATGAA

SEQ ID NO: 13 (see Table 1)
> MT-ND1, FWD primer, CCATTTGCAGACGCCATAAA

SEQ ID NO: 14 (see Table 1)
> MT-ND1, REV primer, GAGTGATAGGGTAGGTGCAATAA

SEQ ID NO: 15 (see Table 1)
> MT-ND1, Probe, AGAACCAATACGCCCTTTAACAACCTCT

SEQ ID NO: 16 (see Table 1)
> HK2, FWD primer, TCAAAGAGAACAAGGGCGAG

SEQ ID NO: 17 (see Table 1)
> HK2, REV primer, AGGAAGCGGACATCACAATC

SEQ ID NO: 18 (see Table 1)
> HK2, Probe, AGAAACATCCCCATTTTGCCAAGCG

SEQ ID NO: 19 (see Table 1)
> SLC2A1, FWD primer, GATTGGTTCCTTCTCTGTCGG

SEQ ID NO: 20 (see Table 1)
> SLC2A1, REV primer, CCCAGGATCAGCATCTCAAAG

SEQ ID NO: 21 (see Table 1)
> SLC2A1, Probe, TTATGGGCTTCTCCAAACTGGGCA

SEQ ID NO: 22 (see Table 1)
> LDHA, FWD primer, GCTCCCCAGAACAAGATTACAG

SEQ ID NO: 23 (see Table 1)
> LDHA, REV primer, TCGCCCTTGAGTTTGTCTTC

SEQ ID NO: 24 (see Table 1)
> LDHA, Probe, AGCTCATCCGCCAAGTCCTTCATT
```

SEQUENCE (amino acid sequence)

```
                                                        SEQ ID NO: 25
MLRAAARFGPRLGRRLLSARKKRRQRRR
```

Other Embodiments

While we have described a number of embodiments, it is apparent that our basic disclosure and examples may provide other embodiments that utilize or are encompassed by the compositions and methods described herein. Therefore, it will be appreciated that the scope of is to be defined by that which may be understood from the disclosure and the appended claims rather than by the specific embodiments that have been represented by way of example.

All references cited herein are hereby incorporated by reference.

---

What is claimed is:

1. A method for allogeneic transplantation of mitochondria in a human subject, said method comprising:
   culturing primary fibroblasts of a human donor without antibiotics, wherein the human donor is a donor other than the subject;
   isolating the donor mitochondria from the primary fibroblasts; and
   administering to said subject a composition comprising the isolated donor mitochondria.

2. The method of claim 1, wherein the subject has a neurodegenerative disease.

3. The method of claim 1, wherein the subject has a disease selected from the group consisting of amyotrophic lateral sclerosis (ALS), Parkinson's disease (PD), a PD-related disorder, Alzheimer's disease (AD), Lewy body dementia (LBD), dementia, muscular dystrophy (MD), a mitochondrial disorder, prion disease, motor neuron disease (MND), Huntington's disease (HD), multiple sclerosis (MS), spinocerebellar ataxia (SCA), spinal muscular atrophy (SMA), Friedreich's ataxia, Batten disease, and fatal familial insomnia.

4. The method of claim 2, wherein the subject has amyotrophic lateral sclerosis (ALS).

5. The method of claim 1, wherein the composition further comprises a mitochondrial storing buffer having a potassium ion concentration safe for administration to humans.

6. The method of claim 1, wherein the administering step comprises parenterally administering at least one-unit dose of said composition to said subject.

7. The method of claim 6, wherein the administering step comprises both intramuscular injection and intravenous injection of said composition to said subject.

8. The method of claim 1, wherein isolating said donor mitochondria comprises preparing cell lysate from primary fibroblasts of the donor via tissue dissociation.

9. The method of claim 1, wherein isolating said donor mitochondria comprises using a mitochondrial isolation buffer comprising a serine protease inhibitor.

10. The method of claim 1, comprising isolating said donor mitochondria without using an antibiotic.

11. The method of claim 1, wherein the donor and the subject are not an HLA (human leukocyte antigen) match.

12. The method of claim 1, wherein the composition administered to the subject does not comprise an antibiotic.

13. The method of claim 1, wherein the isolating step is conducted using a mitochondrial isolation buffer composition.

14. The method of claim 1, further comprising storing the isolated mitochondria at a temperature below −40° C.

15. The method of claim 1, comprising administering to the subject an iron-chelating agent.

16. The method of claim 1, comprising administering to the subject an antioxidant and/or a probiotic.

17. A method for treating a neurodegenerative disease in a human subject in need thereof, said method comprising administering to said subject a composition comprising mitochondria in an amount sufficient to treat said neurodegenerative disease, wherein the composition comprises mitochondria isolated from human primary fibroblasts cultured without antibiotics.

18. A method for treating amyotrophic lateral sclerosis (ALS) in a human subject in need thereof, said method comprising administering to said subject a composition comprising mitochondria in an amount sufficient to treat said ALS, wherein the composition comprises mitochondria isolated from human primary fibroblasts cultured without antibiotics.

19. The method of claim 13, wherein the mitochondrial isolation buffer composition comprises:
   a buffering agent;
   a chelating agent;
   a sugar;
   an agent that acts as a membrane stabilizer or an oxygen radical scavenger or a binder of Ca2+ or a binder of free fatty acid; and
   a serine protease inhibitor.

20. The method of claim 19, wherein the mitochondrial isolation buffer composition does not comprise an antibiotic.

21. The method of claim 19, wherein the buffering agent is a zwitterionic sulfonic acid buffering agent.

22. The method of claim 19, wherein the chelating agent is ethylene glycol-bis(β-aminoethyl ether)-N,N,N',N'-tetraacetic acid (EGTA) or salt thereof.

23. The method of claim 19, wherein the sugar is sucrose.

24. The method of claim 19, wherein the agent that acts as a membrane stabilizer or an oxygen radical scavenger or a binder of Ca2+ or a binder of free fatty acid is bovine serum albumin (BSA).

25. The method of claim 19, wherein the serine protease inhibitor is phenylmethylsulfonyl fluoride (PMSF).

26. The method of claim 1, wherein the composition comprises a suspension of the isolated donor mitochondria.

* * * * *

SEQUENCE LISTING

```
<160> NUMBER OF SEQ ID NOS: 25

<210> SEQ ID NO 1
```

```
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
ctagccgcag gcattactat ac                                              22

<210> SEQ ID NO 2
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
tgtcaaggga tgagttggat aaa                                             23

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
gccgtagccc aaacaatttc                                                 20

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
cgtaacggaa gcgtggataa                                                 20

<210> SEQ ID NO 5
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
ctgagtctcc cttggatctt tg                                              22

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
agggcaggtg aaactgtatg                                                 20

<210> SEQ ID NO 7
<211> LENGTH: 22
```

-continued

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
gaggtatcct gaccctgaag ta                                              22

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
cacacgcagc tcattgtaga                                                 20

<210> SEQ ID NO 9
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
tggcattgtt accaactggg acga                                            24

<210> SEQ ID NO 10
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
accaccatca tttctccttc tc                                              22

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
ctcctgcatg ggctagattt                                                 20

<210> SEQ ID NO 12
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
aagcaggagc aggaacagga tgaa                                            24

<210> SEQ ID NO 13
<211> LENGTH: 20
<212> TYPE: DNA
```

<213> ORGANISM: Artificial Sequence
<220> FEATURE:
<223> OTHER INFORMATION: Description of Artificial Sequence: Synthetic
      oligonucleotide

<400> SEQUENCE: 13
ccatttgcag acgccataaa                                                     20

<210> SEQ ID NO 14
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
gagtgatagg gtaggtgcaa taa                                                 23

<210> SEQ ID NO 15
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
agaaccaata cgcccttta caacctct                                             28

<210> SEQ ID NO 16
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
tcaaagagaa caagggcgag                                                     20

<210> SEQ ID NO 17
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17
aggaagcgga catcacaatc                                                     20

<210> SEQ ID NO 18
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18
agaaacatcc ccattttgcc aagcg                                               25

<210> SEQ ID NO 19
<211> LENGTH: 21
<212> TYPE: DNA
<213> ORGANISM: Artificial Sequence

```
<220> FEATURE:
<223> OTHER INFORMATION: Description of Artificial Sequence: Synthetic
      oligonucleotide

<400> SEQUENCE: 19
gattggttcc ttctctgtcg g                                              21

<210> SEQ ID NO 20
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20
cccaggatca gcatctcaaa g                                              21

<210> SEQ ID NO 21
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21
ttatgggctt ctccaaactg ggca                                           24

<210> SEQ ID NO 22
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 22
gctccccaga acaagattac ag                                             22

<210> SEQ ID NO 23
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 23
tcgcccttga gtttgtcttc                                                20

<210> SEQ ID NO 24
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 24
agctcatccg ccaagtcctt catt                                           24

<210> SEQ ID NO 25
<211> LENGTH: 28
<212> TYPE: PRT
<213> ORGANISM: Artificial Sequence
<220> FEATURE:
```

```
<223> OTHER INFORMATION: Description of Artificial Sequence: Synthetic
      peptide

<400> SEQUENCE: 25

Met Leu Arg Ala Ala Ala Arg Phe Gly Pro Arg Leu Gly Arg Arg Leu
1               5                   10                  15

Leu Ser Ala Arg Lys Lys Arg Arg Gln Arg Arg Arg
            20                  25
```